United States Patent

(12) United States Patent
Luzi

(10) Patent No.: US 11,077,315 B2
(45) Date of Patent: Aug. 3, 2021

(54) METHOD AND SYSTEM FOR MODULATING THE BRAIN ELECTRICAL ACTIVITY

(71) Applicant: POLICLINICO SAN DONATO S.P.A.-ISTITUTO DI RICOVERO E CURA A CARATTERE SCIENTIFICO, San Donato Milanese (IT)

(72) Inventor: Livio Luzi, San Donato Milanese (IT)

(73) Assignee: POLICLINICO SAN DONATO S.P.A.—ISTITUTO DI RICOVERO E CURA A CARATTERE SCIENTIFICO, San Donato Milanese (IT)

(*) Notice: Subject to any disclaimer, the term of this patent is extended or adjusted under 35 U.S.C. 154(b) by 215 days.

(21) Appl. No.: 16/333,172

(22) PCT Filed: Sep. 14, 2017

(86) PCT No.: PCT/IB2017/055557
§ 371 (c)(1),
(2) Date: Mar. 13, 2019

(87) PCT Pub. No.: WO2018/051263
PCT Pub. Date: Mar. 22, 2018

(65) Prior Publication Data
US 2019/0217114 A1 Jul. 18, 2019

(30) Foreign Application Priority Data

Sep. 14, 2016 (IT) .......................... 102016000092729
Mar. 31, 2017 (IT) .......................... 102017000035900

(51) Int. Cl.
A61N 2/00 (2006.01)
A61N 2/02 (2006.01)
A61N 1/36 (2006.01)

(52) U.S. Cl.
CPC ............... *A61N 2/006* (2013.01); *A61N 2/02* (2013.01); *A61N 1/36025* (2013.01)

(58) Field of Classification Search
CPC ....... A61N 2/006; A61N 1/36025; A61N 2/02
See application file for complete search history.

(56) References Cited

U.S. PATENT DOCUMENTS

2006/0287566 A1* 12/2006 Zangen .................. A61N 2/006
600/15
2007/0135859 A1 6/2007 Eriksson et al.
(Continued)

FOREIGN PATENT DOCUMENTS

EP 2357021 A2 8/2011
WO 2006134598 A2 12/2006
(Continued)

OTHER PUBLICATIONS

Madalina Cosmulescu, ORest Bolbocean, Georgiana Mazilu, Karol Borzecki, Cristian Dinu Popescu. "The use of trancranial mangetic stimulation and thermography in the examination of patients with multiple sclerosis." Jun. 29, 2011. New Medicine 2011; 15 (2) pp. 52-56. (Year: 2011).*

(Continued)

Primary Examiner — Christine H Matthews
Assistant Examiner — Joshua Daryl D Lannu
(74) Attorney, Agent, or Firm — Lucas & Mercanti, LLP

(57) ABSTRACT

A deep and repetitive transcranial magnetic stimulation of an individual is performed by applying magnetic pulses at least to a region of the scalp of the individual, the region being at least the bilateral prefrontal cortex, and can include preferably the bilateral prefrontal cortex and can include the insula. A threshold intensity of the magnetic pulses is determined by applying to the individual one or more reference magnetic stimulations, and a reaction of the indi- (Continued)

vidual to the reference stimulation is determined. The reaction corresponds to a right thumb movement. A magnetic stimulation is repeatedly applied for at least 80 trains per session for a duration not exceeding 2 seconds each with a time interval between a train application and the next one not less than 20 seconds, wherein the magnetic stimulation has a frequency of at least 18 Hz with an intensity of stimulation at least 120% of the threshold intensity.

16 Claims, 28 Drawing Sheets

(56) References Cited

U.S. PATENT DOCUMENTS

| | | | |
|---|---|---|---|
| 2007/0260107 A1* | 11/2007 | Mishelevich | A61N 2/004 600/14 |
| 2010/0185042 A1* | 7/2010 | Schneider | A61N 2/02 600/13 |
| 2012/0310035 A1* | 12/2012 | Schneider | A61N 2/02 600/13 |
| 2014/0058189 A1 | 2/2014 | Stubbeman | |
| 2016/0038754 A1 | 2/2016 | Adjouadi et al. | |
| 2016/0339238 A1 | 11/2016 | Ahmed et al. | |

FOREIGN PATENT DOCUMENTS

| | | |
|---|---|---|
| WO | 2007016279 A2 | 2/2007 |
| WO | 2007130308 A2 | 11/2007 |

OTHER PUBLICATIONS

Cosmulescu, et al., "The use of transcranial magnetic stimulation and thermography in the examination of patients with multiple sclerosis", New Medicine, vol. 15, No. 2, 2011, pp. 52-56.

Italian Patent Office Search Report dated May 12, 2017, which was issued in connection with Italian Patent Application No. 102016000092729 (11 pages).

Italian Patent Office Search Report dated Nov. 20, 2017, which was issued in connection with Italian Patent Application No. 102017000035900 (9 pages).

* cited by examiner

METHOD AND SYSTEM FOR MODULATING THE BRAIN ELECTRICAL ACTIVITY

CROSS-REFERENCE TO RELATED APPLICATIONS

This application is a 371 of PCT/IB2017/055557, filed Aug. 3, 2017, which claims the benefit of Italian Patent Application Nos. 102016000092729, filed Sep. 14, 2016 and 102017000035900, filed Mar. 31, 2017.

TECHNICAL FIELD

The present invention relates to a non-therapeutic method and system for a deep and repetitive transcranial magnetic stimulation of an individual as well as to a method and system for modulating the brain electrical activity of an individual through magnetic stimulation. In addition, the present invention relates to the use of such a system. In particular, the invention is directed to modulating the physio-pathological parameters in an individual not connected to addictions, such as drugs or food.

BACKGROUND ART

Repetitive Transcranial Magnetic Stimulation (rTMS) is a non-invasive electromagnetic stimulation technique of the brain tissue of an individual. Induced electrical activity in the brain causes a depolarization of nerve cells, i.e. excites them, resulting in the stimulation (high frequency TMS>1 Hz) or inhibition (low frequency TMS≤1 Hz) of the brain activity for a few milliseconds.

The rTMS technique uses an instrument called "stimulator" which supplies electricity to a magnetic coil which generates a magnetic field in the brain for a short time. The magnetic field produced by the coil goes through the scalp up to the brain without any dispersion and in an almost painless manner and can therefore reach the underlying brain structures, particularly the cerebral cortex, and change the electrical activity thereof in order to improve symptoms of some diseases, such as depression and OCD. The coil is placed on the individual's head in such a way as to allow the magnetic field to reach the brain region of interest. The effects of TMS depend on a number of factors related to the characteristics of the magnetic field, the strength of the field itself, the shape of the coil used for stimulating and the position in which this is placed.

Scientific research has shown an interesting use of rTMS also for the treatment of addictions to substances like alcohol, nicotine and cocaine, proving the effectiveness in reducing the craving and therefore the consumption of the substances themselves. In this case, the magnetic stimulation must act in deeper areas of the brain (such as 3-4 cm of depth from the scalp) (dTMS).

To date, scientific research has focused mainly on the analysis of applications of deep rTMS for individuals subject to addictions and/or neurological and neuropsychiatric disorders (Dinur-Klein L. et al. *Biol Psychiatry* 76:742-9, 2014; Mishra B R. et al. *J. Neuropsychiatry ClinNeurosci* 27: e54-9, 2015; Terraneo A. et al. *EurNeuropsychopharmacol*. 26: 37-44, 2016; *Walsh and Cowey Nat Rev Neurosci*. 2000 October; 1(1):73-9). From the point of view of the equipment used, various systems and equipment have been employed, configured to obtain a more and more effective deep transcranial magnetic stimulation.

In particular, WO 2006/134598 describes a system and a method for transcranial magnetic stimulation comprising a magnetic coil for deep stimulation. Specifically, the coil is configured to minimize the involuntary stimulation of certain parts of the brain by reducing the accumulated surface charge.

WO 2014/128631 describes a TMS system having a coil configured for the stimulation of specific regions of the medial or lateral brain. This system is used in many ways for the treatment of various diseases or addictions such as depression, bipolar disorder, schizophrenia, autism, Parkinson's disease, epilepsy, eating disorders (bulimia, anorexia), alcoholism, gambling addiction, etc.

WO 2013/121359 describes the use of TMS to modulate the blood brain barrier. On the basis of a particular application mode and protocols, it is possible to treat brain cancer by increasing the permeability of said barrier.

However, the prior art does not describe the application of rTMS in different fields, such as the regulation of metabolism or the sympathetic nervous system of an individual regardless of whether this is prone to addictions or particular habits, nor it has assessed the specific modes for the functioning of this technique in these areas.

Therefore, it is the object of the present invention to provide a method and system for the application of rTMS in fields other than those mentioned above.

DESCRIPTION OF THE INVENTION

These objects are achieved by a method, system and use of such a system according to the claims at the end of the present description.

The method according to the present invention is used for modulating the brain electrical activity of an individual through a magnetic stimulation of at least one area of the scalp of said individual. Magnetic stimulation consists of pulses or magnetic stimuli and is adapted to affect control centers or neuronal circuits localized in the brain with systemic consequences.

In particular, the method according to the present invention is not directed to reduce the addiction of the individual from a specific substance or habit.

Specifically, the method initially comprises the determination of a threshold intensity of magnetic pulses as a function of the individual's reaction to a reference magnetic stimulation and subsequently the repeated application of magnetic stimulation at a pulse frequency greater than or equal to 1 Hz, with an intensity higher than said threshold intensity.

This method can be used without any therapeutic effect but may, alternatively or in combination with non-therapeutic use, be used to treat a medical condition of an individual. In particular, it was noted that the method according to the present invention can be used to influence control centers or neuronal circuits localized in the brain of an individual regardless of whether he/she is affected or not by a particular disease.

According to the present invention, the individual is subjected to repetitive transcranial magnetic stimulation (rTMS). In particular, magnetic pulses are generated in one or more regions of the head or scalp of the individual. The application is carried out by a suitable apparatus having the shape of a helmet which is worn by the individual.

Before being subjected to magnetic stimulation, some sort of calibration must be carried out in order to determine a threshold intensity to be taken as reference intensity for the subsequent application of rTMS. Magnetic stimulation is then carried out at a frequency greater than or equal to 1 Hz with an intensity greater than the threshold. In this way, a modulation of the brain electrical activity can be carried out even in fields other than those known.

In one embodiment of the invention, the repeated application of magnetic stimulation influences the regulation of glucose metabolism, resulting in a reduction in the individual's levels of blood glucose.

In an advantageous and focused manner, without resorting to drugs of any kind having unwanted side effects, it is thus possible to regulate the glucose metabolism of an individual.

In a further embodiment of the invention, the repeated application of magnetic stimulation influences the regulation of the activity of the sympathetic nervous system, possibly resulting in a change in the level of hormones such as insulin, leptin, adrenaline, noradrenaline and ghrelin of the individual.

In this way, many physiological processes can be controlled, such as metabolism or the cardiovascular activity, high blood pressure, diabetes, etc.

In order to determine the threshold intensity, magnetic stimulation is applied in the scalp area corresponding to the primary motor cortex at regular intervals, gradually decreasing the intensity of said reference stimulation.

In one embodiment of the invention, in order to obtain a localized stimulation in certain areas of the individual's brain, the repeated application of magnetic stimulation occurs at a frequency of at least 18 Hz with a stimulation intensity corresponding to 120% of the threshold intensity.

Advantageously, in the case of a stimulation at a frequency of 18 Hz, the repeated application of magnetic stimulation comprises at least 80 trains of applications per session, each train of a duration not higher than 2 seconds with an interval of time between one train of application and the next one not smaller than 20 seconds.

According to one embodiment of the invention, the magnetic stimulation is applied on an area of the individual's scalp to influence the brain region corresponding to the bilateral prefrontal cortex, preferably to the bilateral prefrontal cortex and the insula. In this way, the cortical regulation level involved in the regulation of the "dopaminergic reward system" which is activated in response to food-related stimuli (hedonic hunger) can be controlled.

In one embodiment of the invention, the magnetic stimulation is applied on an area of the individual's scalp to indirectly influence the brain area corresponding to the arcuate nucleus, inducing electric currents in that area by the stimulation of the prefrontal cortex or the prefrontal cortex and the insula. In this way, the level of hypothalamic regulation of appetite, involved in the integration of peripheral, cerebral and endocrine signals and consequently in the homeostatic regulation (metabolic hunger) can be controlled.

The system for modulating the brain electrical activity to influence control centers or neuronal circuits localized in the brain with systemic consequences according to the present invention comprises stimulation means for the generation and application of repeated magnetic stimulation consisting of magnetic impulses, wherein said means comprise a magnetic pulse generator and stimulating elements placed on at least one area of the head of an individual and management and control means for the management and control of magnetic stimulation.

In particular, the system is not directed to reduce the addiction of the individual from a specific substance or habit. In addition, the system is configured to initially determine a threshold intensity of magnetic stimulation and to subsequently apply the repetitive magnetic stimulation at a pulse frequency greater than or equal to 1 Hz with an intensity higher than said threshold intensity.

This system allows a modulation of the brain electrical activity of an individual even in fields other than those known in the literature.

According to one embodiment of the present invention, the stimulation means comprise at least one "H" shaped coil for deep transcranial magnetic stimulation. This special shape of the coil allows a deep and localized magnetic stimulation in precise areas of the individual's brain.

According to a further embodiment of the present invention, the system further comprises an infrared thermography unit for controlling the skin temperature and means for measuring the movement of the individual, i.e. his/her physical activity, such as an accelerometer.

In particular, the stimulation means are configured to generate a magnetic stimulation at a pulse frequency of at least 18 Hz with a stimulation intensity corresponding to 120% of the threshold intensity.

Moreover, the control and management means are configured to carry out the magnetic stimulation comprising at least 80 trains of applications per session, each train of a duration not higher than 2 seconds with an interval of time between one train of application and the next one not smaller than 20 seconds.

The system according to the present invention may have different applications.

In particular, the system may be used for the regulation of glucose metabolism, resulting in a reduction in the individual's levels of blood glucose.

In addition or alternatively, the system according to the present invention may be used for the regulation of the activity of the sympathetic nervous system, resulting in a change in the level of hormones such as insulin, leptin, adrenaline, noradrenaline and ghrelin of the individual.

In addition or alternatively, the system according to the present invention may be used for the regulation of the body temperature, also through an activation of brown fat.

In addition or alternatively, the system according to the present invention may be used for the regulation of the motor activity of the individual by promoting the release of dopamine at a striatal level.

In addition or alternatively, the system according to the present invention may be used for the modulation of pituitary hormones (prolactin and TSH thyroid-stimulating hormone) potentially useful in case of benign neuroendocrine tumors or central dysthyroidism, respectively.

In addition or alternatively, the system according to the present invention may be used for the modulation of the activity of the sympathetic nervous system to lead to an increase in the level of physical activity of the individual.

In addition or alternatively, the system according to the present invention may be used to alter the intestinal bacteria, the so-called "microbiota", promoting a weight loss in obese individuals.

The possible role played by the intestinal microbiota in the pathogenesis of obesity has been proven by several studies. The composition of the intestinal microbiota in obese individuals is characterized by a decrease in the abundance of bacteria which produce short-chain fatty acids (SCFA), such as *Bacteroides*, Blautia, Butyricoccus and Phascolarctobacterium.

In particular, an alteration of the intestinal microbiota may promote obesity through a variety of mechanisms:
- increased energy production by specific microbes;
- increased intestinal permeability with translocation of bacteria or bacterial endotoxin components in the active metabolic tissues;
- alteration of satiety/appetite-inducing signal release;
- altering the production of neurotransmitters of intestinal microbes.

Communication between the brain and the intestinal microbiota is bidirectional and is mediated by various communication pathways which include the hypothalamic-pituitary-adrenal (HPA) axis and certain neurotransmitters involved in the food reward system.

The repetitive action of TMS affects the modulation of the intestinal microbiota composition through an action on the pituitary hormones and on neurotransmitters.

In this way, a significant loss of body weight can be achieved which improves the insulin sensitivity, the sympathetic nervous system activity and the composition of the intestinal microbiota, promoting bacterial species with anti-inflammatory properties, representative of a healthy subject. At the same time, several hormonal and metabolic parameters improve—levels of glucose, insulin, pituitary hormones and norepinephrine—which play a key role both in the regulation of hunger stimulus and in the composition of the microbiota.

The system can be used to reduce the food craving and food intake and consequently the body weight also in obese people. State-of-the-art approaches to treat obesity include life-style interventions (diet and physical activity programs) supported by psychological and behavioral interventions to overcome the unwillingness of obese people to undergo dietary and exercise programs. In order to ameliorate patients' compliance, pharmacological treatment is considered part of a comprehensive strategy of obesity management. Bariatric surgery, however, currently represents the most effective treatment for morbid obesity in terms of long-term weight loss, improvement of quality of life and decrease of overall mortality. Nonetheless, bariatric surgery is considered a major surgical intervention with significant risks of perioperative mortality. In addition, the emergence or re-emergence after bariatric surgery of a binge eating disorder, and a loss of eating control results in reduced weight loss and/or increased weight regain.

Obesity is a heterogeneous condition not classified as an eating disorder, but which may be both a risk factor for, and a consequence of the latter. Considering several common behavioral and neurobiological mechanisms, there is increasing interest in the conceptualization of disordered eating as a food addiction. Several brain regions appear to be involved in the mechanisms of food craving. An increased activity in the left dorsolateral prefrontal cortex (DLPFC) has been found in food-addicted patients while making decisions about food ingestion, thus suggesting that DLPFC could play a role in regulatory control over food consumption. Most data suggest a dysfunctional inhibitory control and decision-making ability in obese subjects, primarily related to an abnormal brain function of the prefrontal cortex (PFC). Moreover, altered activities in the reward circuitry have also been reported in obese subjects similar to drugs addiction. Several studies suggest that eating palatable food increases activation in reward regions, and causes dopamine (DA) release in the dorsal striatum. The reduced striatal DA D2 receptor availability, and the inferior striatal responsivity to the taste of high-calorie beverages, observed in obese versus lean adults, have led to the hypothesis that obese subjects have a lower sensitivity of DA-based regions and seek overeating to compensate for this deficiency.

BRIEF DESCRIPTION OF THE DRAWINGS

A complex and highly coordinated system of peripheral appetite hormones and centrally mediated neuronal regulation is also involved in body weight homeostasis. Perturbations in the gut-brain axis involving hormones like leptin, ghrelin, insulin, glucagon, glucagon like peptide-1 (GLP-1), neuropeptide Y (NPY) could play a role in the pathophysiology of obesity. Abnormalities in the food reward system may be associated with emotional and physiological stress.

These and other aspects of the present invention will become apparent in the light of the following description of some preferred embodiments described hereinafter.

FIG. 1 shows a flowchart of a method 100 for modulating the brain electrical activity of an individual. Method 100 initially comprises the action of providing 102 a system for the deep repetitive transcranial magnetic stimulation (rTMS). The stimulation is carried out by sending magnetic pulses at one or more regions of the brain of an individual.

Figure 1:
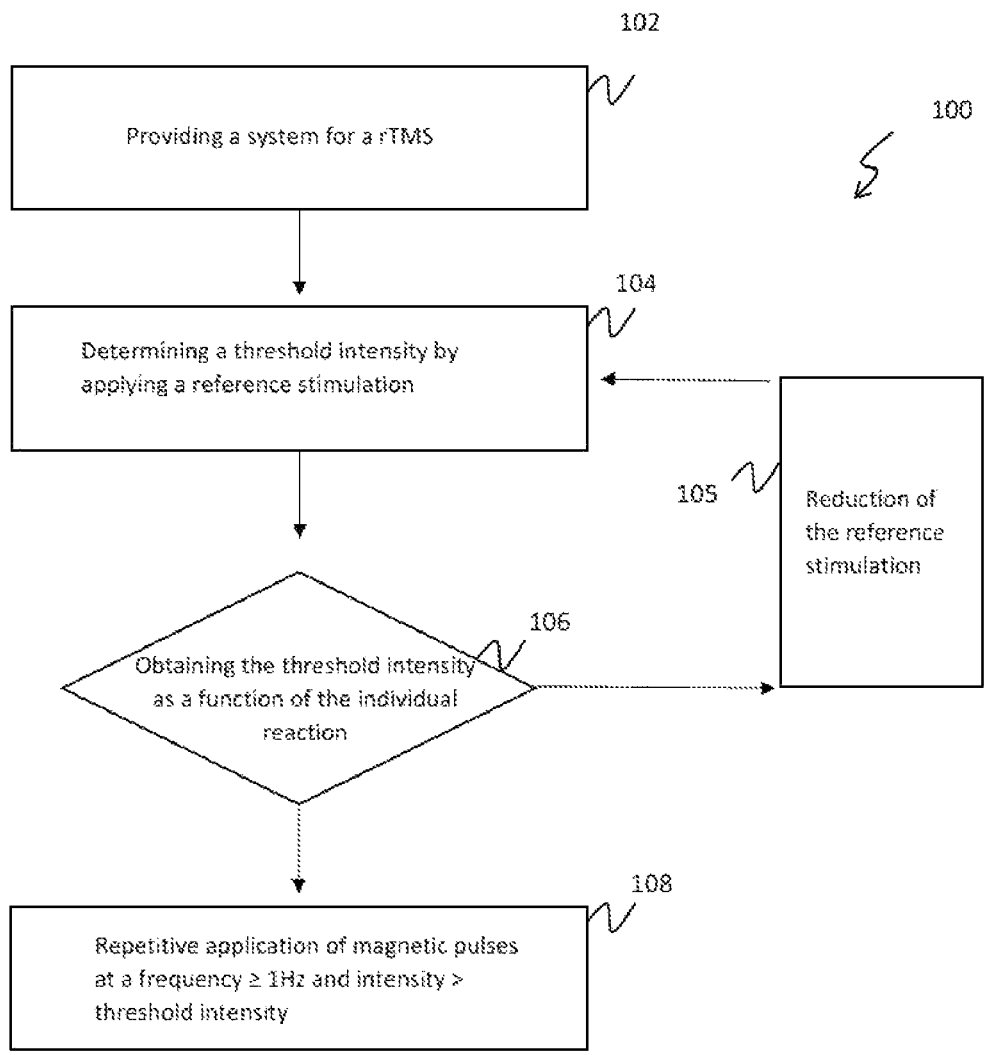
FIG. 1 shows a flowchart of a method for modulating the brain electrical activity according to the present invention.

Before proceeding with the actual repeated stimulation, the method comprises the action of determining 104 a threshold intensity by applying a reference stimulation in a specific region of the scalp of an individual. The threshold intensity is obtained as a function of the individual's reaction to the reference stimulation 106. If the threshold intensity has not been reached, the reference stimulation is decreased 105 and an attempt to determine such a threshold 104 again is made. If the threshold intensity has been reached, method 100 continues with the repeated application of magnetic stimulation 108 according to the parameters provided by method 100.

Figure 2:
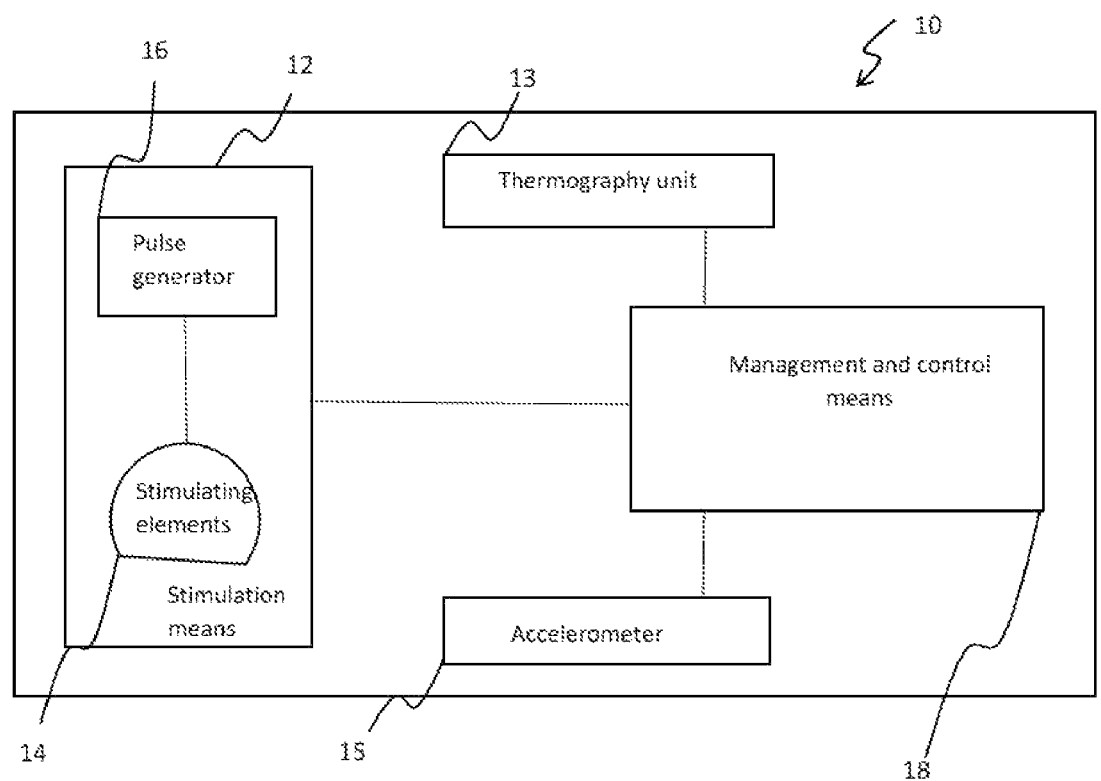
FIG. 2 shows a block diagram of a system for modulating the brain electrical activity according to the present invention.

FIG. 2 shows a schematic representation of a system 10 for modulating the brain electrical activity. System 10 comprises stimulation means 12 for the generation and application of magnetic stimulation and management and control means 18 for the management and control of magnetic pulses.

In particular, the stimulation means 12 comprise at least one magnetic pulse generator 16 and stimulating elements 14 placed in certain positions of the individual's scalp. Specifically, said elements 14 may take the form of a helmet to be applied on the head of the individual.

Moreover, system 10 comprises an infrared thermography unit 13 and means for measuring the movement 15, such as an accelerometer.

Below are the methods of treatment carried out on a number of individuals and the results obtained.

Data and Methods

Transcranial magnetic stimulation according to the present invention can be used in the treatment of diabetes mellitus and can be evaluated at the same time in a study to evaluate the effectiveness of deep rTMS on satiety and on weight control.

With regard to the application of TMS on the modification of the microbiota, at least the following diseases are affected in addition to obesity: type 2 diabetes, type 1 diabetes, autoimmune diseases, inflammatory bowel diseases, including chronic, colon neoplasms, liver neoplasms, cardiovascular diseases associated with dyslipidemia, some forms of anemia and neurodegenerative diseases.

A randomized, prospective, double-blind, placebo-controlled study was proposed. This study was conducted at the clinics of Endocrinology and Metabolic Disease Area, IRCCS Policlinico San Donato, San Donato Milanese (MI), in the period between 2015 and 2016 and confirmed in 2017. The study was approved by the Ethics Committee of the Hospital San Raffaele and funded by the Ministry of Health, and was conducted according to good clinical practice guidelines and in accordance with the Helsinki Declaration.

Patients

Adults (aged between 22 and 68) who went at the Policlinico San Donato requiring a treatment for obesity were considered for the study. Patients with a body mass index (BMI) of between 30-45 kg/m2 were included in the study. Exclusion criteria were considered: family and personal medical history of convulsions, psychiatric disorders, neurological disorders, presence of implanted metal devices, basal glycaemia levels>150 mg/dl, substance abuse (with the exception of nicotine), use of medications for the treatment of obesity or drugs able to change the body weight, use of drugs able to change the motor threshold, pregnant or nursing women, patient with history of neurosurgery or affected by clinically unstable diseases.

During the trial, deep rTMS was the only treatment allowed for obesity.

Patients were randomized into 5 different groups, intended to receive high frequency (18 Hz), low frequency (1 Hz) or placebo treatment, with or without food-related stimulus (Table 1)

TABLE 1

Treatment groups

| | REAL Frequency | | | | PLACEBO |
|---|---|---|---|---|---|
| | 18 Hz (high frequency) | | 1 Hz (low frequency) | | 18 or 1 Hz |
| Time | 29.3 minutes | | 43 minutes | | 29.3 or 43 minutes |
| Stimulus | Present | Absent | Present | Absent | Present |
| Group name | 18+ | 18− | 1+ | 1− | 0+ |
| Number of patients: | 5 | 5 | 3 | 3 | 5 |

21 patients completed the study out of 24 randomized patients. Three patients discontinued the study, two for personal reasons and one patient for having blood glucose values >150 mg/dl. The 3 patients who discontinued the study were not considered in the statistical analysis.

By using the TMS for changing the intestinal microbiota, fourteen obese individuals were selected (three male and eleven female) with an age of 45.4±10.0 years and a body mass index BMI=38.3±5.4 Kg/m$^2$.

The individuals were randomly divided in two groups and received fourteen sessions (three times per week in five weeks) of TMS or sham. Regarding the individuals' selection, individuals with an age comprised between 22 and 65 years, a BMI comprised between 30 e 45 Kg/m$^2$ and willingness to reduce the body weight were considered. On the other hand, pregnant or nursing women, individuals with psychiatric or brain disorders, with drugs or alcohol addiction with personal or familiar epilepsy problems or subjected to pharmacological treatments for light epilepsy and individuals with metallic implants were excluded.

By using the TMS for the reduction of the food craving and body weight in obese people, 39 patients were selected. Out of 39 enrolled patients, 33 subjects (10 males and 23 females) completed the study as per the protocol. The six participants who dropped out the study were excluded from statistical analysis. The mean age of the sample group was 46.0±1.6 years and the mean BMI was 36.5±0.8 kg/m2.

Patients fulfilling all inclusion/exclusion criteria were allocated to one of 3 experimental groups (Table 2).

TABLE 2

Treatment Groups

| | REAL | | SHAM |
|---|---|---|---|
| Frequency | 18 Hz (high) | 1 Hz (low) | 18 or 1 Hz |
| Duration | 29.3 minutes | 43 minutes | 29.3 or 43 minutes |
| Group Name | HF | LF | Sham |
| Patients Number | 15 | 9 | 9 |
| Food Cue | Present HF (cue) | Absent LF (no cue) | Present LF (cue) | Absent LF (no cue) | Present |
| Patients Number | 8 | 7 | 4 | 5 | 9 |

Deep TMS stimulation conditions could either be high-frequency (HF, 18 Hz group), low-frequency (LF, 1 Hz group) or sham (Sham group). Fifteen obese subjects were allocated in HF group, 9 in LF group, and 9 in Sham group. Obese subjects belonging to HF and LF groups were either shown a series of palatable food images (cue) or not (no cue); the patients in the Sham group were all exposed to the cue.

At baseline, no significant differences in age and BMI were found among the three groups (Table 3).

1) Chronic Study. Each patient received 15 dTMS sessions, 3 times per week, in 5 weeks (visit 1-15). Follow-up visits were planned 1 month (FU1) and 6 months (FU2) after the end of the treatment. Fourteen out of the 33 enrolled patients underwent an evaluation 1 year after the end of the treatment (FU3). 2) Acute Study. On visit 1 and visit 15 (last day of the 5-week treatment), all patients underwent blood collection at the beginning and at the end of the dTMS procedure for further analysis, as described in the following.

Out of the 39 enrolled patients, 3 patients dropped out for personal reasons, 1 patient was excluded from the study because a level of fasting blood glucose greater than 150 mg/dL was detected, 1 patient discontinued the treatment due to high blood pressure and 1 patient due to an incidental post-traumatic fracture of the right shoulder. Three dropout patients belonged to HF and the other 3 belonged to LF. Dropout patients were excluded from the statistical analysis.

TABLE 3

Baseline characteristics of the participants

| | Unity of measure | HF (n = 15) | LF (n = 9) | Sham (n = 9) | p-value |
|---|---|---|---|---|---|
| Age, years | years | 45.9 ± 2.2 | 44.6 ± 3.5 | 47.6 ± 3.2 | 0.798 |
| Gender | males/females | 6/9 | 2/7 | 2/7 | — |
| BMI | kg/m² | 36.4 ± 1.3 | 37.5 ± 2.1 | 35.7 ± 0.9 | 0.729 |
| Food craving | | | | | |
| FCQ-T Score | — | 126.1 ± 10.6 | 120.6 ± 14.9 | 116.8 ± 12.7 | 0.861 |
| Body composition | | | | | |
| FM | % | 46.9 ± 4.8 | 49.9 ± 7.5 | 46.0 ± 5.3 | 0.592 |
| FFM | % | 53.1 ± 5.3 | 50.1 ± 7.5 | 54.0 ± 6.2 | 0.593 |
| FM | kg | 48.8 ± 5.3 | 53.6 ± 8.7 | 44.5 ± 5.1 | 0.238 |
| FFM | kg | 55.8 ± 6.1 | 53.1 ± 8.1 | 50.2 ± 6.5 | 0.584 |
| Metabolism Analysis | | | | | |
| REE | % | 93.6 ± 3.1 | 94.4 ± 4.2 | 93.3 ± 3.9 | 0.982 |
| RQ | — | 0.86 ± 0.01 | 0.88 ± 0.02 | 0.86 ± 0.02 | 0.578 |
| Blood pressure | | | | | |
| SBP | mmHg | 124.6 ± 2.9 | 113.1 ± 4.3 | 121.1 ± 2.6 | 0.061 |
| DBP | mmHg | 82.3 ± 1.8 | 71.9 ± 4.4 | 73.3 ± 4.1 | 0.049 |
| Heart rate | pulses/min | 82.6 ± 2.3 | 82.7 ± 3.1 | 78.2 ± 2.6 | 0.442 |
| Physical activity | | | | | |
| TEE | kcal/day | 2188.5 ± 106.1 | 2100.8 ± 58.2 | 1874.0 ± 50.8 | 0.087 |
| AEE | kcal/day | 216.0 ± 29.5 | 238.5 ± 38.9 | 255.4 ± 47.6 | 0.750 |
| Very mild PAT | min/day | 911.6 ± 55.5 | 947.3 ± 46.4 | 746.0 ± 78.9 | 0.103 |
| Mild PAT | min/day | 15.1 ± 3.3 | 17.3 ± 3.7 | 18.8 ± 4.5 | 0.782 |
| Moderate PAT | min/day | 3.2 ± 1.2 | 2.3 ± 1.0 | 4.4 ± 1.6 | 0.587 |
| Intensive PAT | min/day | 0.0 ± 0.0 | 0.0 ± 0.0 | 0.2 ± 0.2 | 0.581 |
| METs | — | 1.6 ± 0.1 | 1.6 ± 0.2 | 1.7 ± 0.2 | 0.710 |
| Steps | steps/day | 5085.3 ± 758.7 | 5507.5 ± 1042.9 | 6687.2 ± 1293.8 | 0.530 |
| Kilometers | km/day | 3.4 ± 0.5 | 3.8 ± 0.7 | 4.5 ± 0.9 | 0.501 |

TABLE 3-continued

Baseline characteristics of the participants

| | Unity of measure | HF (n = 15) | LF (n = 9) | Sham (n = 9) | p-value |
|---|---|---|---|---|---|
| Metabolic parameters | | | | | |
| Glucose | mg/dL | 87.9 ± 4.3 | 103.6 ± 11.3 | 94.7 ± 6.0 | 0.280 |
| Insulin | μU/mL | 20.1 ± 5.2 | 30.8 ± 9.8 | 19.5 ± 5.1 | 0.453 |
| HOMA-IR | — | 4.9 ± 1.5 | 8.9 ± 3.7 | 4.6 ± 1.3 | 0.367 |
| Glucagon | pg/mL | 42.6 ± 4.1 | 30.5 ± 4.3 | 40.9 ± 4.1 | 0.328 |
| Cholesterol | mg/dL | 197.4 ± 8.9 | 207.7 ± 19.9 | 190.2 ± 6.1 | 0.650 |
| Triglycerides | mg/dL | 155.4 ± 31.2 | 174.9 ± 39.2 | 105.7 ± 13.6 | 0.355 |
| Fructosamine | μmol/L | 235.2 ± 6.4 | 227.3 ± 11.1 | 236.2 ± 10.8 | 0.771 |
| Glycated hemoglobin | mmol/mol | 36.3 ± 4.8 | 41.0 ± 8.4 | 34.8 ± 6.2 | 0.547 |
| HPA-axis hormones | | | | | |
| TSH | μUI/mL | 2.72 ± 0.28 | 2.68 ± 0.59 | 3.14 ± 0.59 | 0.758 |
| Prolactin | ng/mL | 17.1 ± 1.3 | 15.8 ± 2.0 | 15.0 ± 2.5 | 0.704 |
| FSH | mUI/mL | 16.5 ± 6.3 | 15.9 ± 5.8 | 23.6 ± 8.4 | 0.722 |
| LH | mUI/mL | 10.7 ± 3.2 | 12.6 ± 4.3 | 15.9 ± 4.3 | 0.624 |
| ACTH | pg/mL | 27.3 ± 3.5 | 28.1 ± 2.8 | 27.8 ± 3.5 | 0.986 |
| Cortisol | μg/dL | 0.39 ± 0.06 | 0.35 ± 0.05 | 0.39 ± 0.05 | 0.814 |
| Neuropeptides | | | | | |
| Ghrelin | ng/mL | 13.5 ± 3.0 | 14.9 ± 2.9 | 13.6 ± 4.4 | 0.746 |
| Leptin | ng/mL | 66.9 ± 10.3 | 80.7 ± 17.3 | 104.2 ± 39.5 | 0.480 |
| Epinephrine | pg/mL | 359.7 ± 55.4 | 290.5 ± 38.7 | 415.3 ± 125.6 | 0.577 |
| Norepinephrine | ng/mL | 5.4 ± 1.1 | 5.3 ± 0.7 | 5.0 ± 0.9 | 0.803 |
| β-endorphin | ng/mL | 0.299 ± 0.05 | 0.424 ± 0.06 | 0.366 ± 0.07 | 0.296 |

Stimulation Procedure

Deep rTMS was carried out using a magnetic stimulator Magstim Rapid2® (The Magstim Co. Ltd., Whitland, Carmarthenshire, United Kingdom) provided with an H-shaped coil, used specifically in the treatment of addictions, able to stimulate deeper brain areas (up to 3 cm from the scalp rather than 1.5 cm), such as the insula and the prefrontal cortex (PFC). Before the stimulation, the patient was instructed to wear earplugs because of the noise produced during the treatment, and was subjected to the procedure for determining the rest motor threshold (RMT). It was determined on the left primary motor cortex by using the display method and the maximum likelihood strategy. Once the point of the scalp where the best movement of the adductor muscle pollicis brevis of the right hand was observed had been determined, we proceeded to the determination of RMT by applying individual stimuli every 5 seconds at the level of the motor cortex and gradually decreasing the intensity. "Motor threshold" is the lowest intensity of stimulation needed to produce a movement of the right thumb.

Cueing Procedure

In half of the patients belonging to groups 18 and 1, and in all the patients in the sham group, achieving a growing craving for food was induced by showing, prior to treatment, pictures of food previously identified as favorites by the patients. Depending on the randomization code, low- or high-frequency rTMS sessions were administered, designed to stimulate the insula and the PFC bilaterally. All treatments were carried out 3 times a week for 5 consecutive weeks (15 total sessions).

Stimulation Characteristics

Low frequency (1 Hz) stimulation intensity: 120% of RMT, train of stimulation time: 10 minutes, interval between trains: 1 minute, number of trains: 4, total number of pulses: 2400, duration of treatment: 43 min.

High frequency (18 Hz) stimulation intensity: 120% of RMT, train of stimulation time: 2 seconds, interval between trains: 20 seconds, number of trains: 80, total number of pulses: 2880, duration of treatment: 29.3 min.

All patients received 15 rTMS sessions, 3 times a week for 5 consecutive weeks. Two follow-up visits were scheduled 1 and 6 months away from the end of the treatment, respectively. All patients were instructed to follow a food plan during the entire duration of the study.

Glucose Metabolism

To assess the glucose metabolism, all patients were subjected to the following blood tests:
blood glucose, insulin, fructosamine, calculation of the HOmeostatic Model Assessment of Insulin Resistance (HOMA-IR)

Blood glucose and insulin were tested at the following times: T0 (baseline, before the first session of rTMS), T1 (immediately after the first rTMS session), T2 (before the last rTMS session), T3 (immediately after the last rTMS session), FU1 (1 month after the last rTMS session) and FU2 (6 months after the last rTMS session).

Calculating the HOMA-IR was carried out at the following times: T0, T1, T2, T3, FU1, FU2.

Fructosamine was tested at the following times: T0, T2, FU1 and FU2.

Neuroendocrine Structure

The following parameters were considered to assess the neuroendocrine structure:
ACTH, LH, FSH, GH, TSH, prolactin, cortisol, ghrelin, leptin, beta-endorphins, adrenaline, noradrenaline.

These parameters were tested at the following times: T0, T1, T2, T3, FU1 and FU2.

Body Temperature

The body temperature was measured in the abdomen and nail bed of both hands. It was detected using infrared thermography. In this study, we used a thermal imaging camera model G120EX with the following technical specifications:

Thermal resolution 0.04° C. (with image average)
Measuring accuracy ±2° C. or ±2% of reading
VOx microbolometer "Dual Layer" sensor
Thermal imaging pixels 320 (H)×240 pixels (V)
Spectral range 8 to 14 μm
Image frequency 60 Hz
Field of view 32° (H)×24° (V)
Spatial resolution 1.78 mrad
Focusing range from 10 cm to infinity
14-bit image digitization
Autofocus included
Emissivity temperature correction, distance, reflection, room temp.
Operating temperatures from −15° C. to +50° C.

The recording was carried out before the first rTMS session (T0), immediately after the first rTMS session (T1), before the 15th and last rTMS session (T2) and immediately following the 15th rTMS session (T3).

The skin temperature was measured at the level of the nail bed of both hands, and in the abdomen. In some cases at time T0 and T1, the temperatures were measured at the level of the interscapular region where the brown fat resides, metabolically active.

Physical Activity

Physical activity was monitored during 5 weeks of treatment with rTMS through the Actigraph method, which quantifies the calories consumed daily based on the physical activity recorded. Actigraph is an accelerometer commonly used in research on physical activity (Gorman et al., 2014). The recorded data are quantified by minute and they reflect the acceleration, thus the intensity of physical activity. The higher the scores per minute, the higher the acceleration of motion measured. The thresholds used to determine the different intensity of physical activity were obtained from validated studies and are mainly defined in terms of absolute intensity as Metabolic Equivalents of Task (METs) (Gorman et al., 2014). From the screening visit, each patient wore an Actigraph accelerometer on the belt which was held in place during the entire 5 weeks of treatment. The recorded data were downloaded to a personal computer and processed by the FitMate software (FitMate®, COSMED, Italy).

Microbiota

The following parameters were evaluated to assess the intestinal microbiota:
body weight, evaluated at the beginning and after five weeks of TMS treatment;
neuroendocrine and metabolic parameters, evaluated at the beginning and after five weeks of TMS treatment;
analysis of the intestinal microbiota, evaluated from stool samples collected at the beginning and after five weeks of TMS treatment. The total bacterial DNA was extracted from stool samples using the QIAamp DNA Stool Mini Kit (Qiagen, Italy) and analyzed using a metagenomic approach (Ion Torrent Personal Genome Machine).

Analysis of the Microbiota

Stool samples of fourteen subjects were collected before and after treatment and stored at −20° C. before being analyzed and the total DNA was extracted from the samples according to the instructions of the QIAamp DNA Stool Mini kit manufacturer (Qiagen, Italy).

Partial 16S rRNA gene sequences were amplified from the DNA extracted using the Metagenomic 16S Kit (Life Technologies, Italy) which is designed for rapid analysis of polybacterial samples using the sequential Ion Torrent technology. The Kit includes two sets of primers which selectively amplify the corresponding hypervariable regions of 16S region in bacteria: primer sets V2-4-8 and primer sets V3-6, 7-9. The PCR conditions used are 10 minutes at 95° C., 30 cycles of 30 seconds at 95° C., 30 seconds at 58° C. and 20 seconds at 72° C., followed by 7 minutes at 72° C. Amplification is performed using a SimpliAmp thermocycler (Life Technologies, Italy). The integrity of the PCR amplicons was analyzed by electrophoresis on 2% agarose gel.

PCR products derived from the amplification of hypervariable regions of specific 16S rRNA genes were purified with a purification step which involves Agencourt AMPure XP DNA purification beads (Beckman Coulter Genomics, Germany) in order to remove dimerized primers. The DNA concentration of the amplified sequence library was estimated by the Qbit system (Life Technologies, Italy). Starting from the concentration and the average size of each amplicon, the amount of DNA fragments per microliter was calculated and libraries were created using the Ion Plus Fragment Library kit (Life Technologies, Italy). Barcodes were further added to each sample using the Ion Xpress Barcode Adapters 1-16 kit (Life Technologies, Italy). The PCR emulsion was created using the Ion OneTouch TM400 Template kit (Life Technologies, Italy) according to the manufacturer's instructions. The sequencing of amplicon libraries was carried out on a chip 318 using the Ion Torrent Personal Genome Machine (PGM) system and using the Ion PGM Hi-Q kit (Life Technologies, Italy) according to the manufacturer's instructions. After sequencing, readings of individual sequences were filtered by the PGM software to remove low-quality and polyclonal sequences. The sequences corresponding to the adapter PGM 3' were also automatically deleted. The 16 rRNA sequences were then analyzed by the Ion Reporter Software program which comprises a set of bioinformatics tools which optimize and simplify semiconductor-based sequencing data analysis. The workflow module 16S rRNA in the Ion Reporter Software program was able to classify individual readings by combining a Basic Local Alignment Search Tool (BLAST) alignment with the Greengenes database containing more than 400,000 documents, with a BLAST alignment with the MicroSEQ ID premium database, a high-quality library of complete 16S rRNA sequences. In the first stage, the readings are aligned with the MicroSEQ ID library with each unaligned reading subjected to a second alignment with the Greengenes database to obtain a quick and comprehensive identification of bacteria. The end result of the Ion Reporter Software program was the identification and abundance of microorganisms at phylum, class, family and genus level.

Food Craving

Diet and Lifestyle Recommendations

During the entire study, all subjects were prescribed a hypocaloric diet. The energy requirement was calculated by the dietitian based on the measured basal metabolic rate (via indirect calorimetry) and the physical activity of each subject identified at the Screening visit. 300 kcal/day were subtracted from this amount of energy to obtain the recommended hypocaloric diet. The daily dietary intake included approximately 45% to 50% calorie intake from carbohydrate, up to 30% of calories from fat, and 20% to 25% of calories from protein. At each follow-up visit, the dietitian confirmed the reduction of food intake with a direct interview.

The subjects were also instructed to have moderate-intensity physical activity (e.g., 30 min walking every day).

Measurements

Psychiatric and Psychological Evaluation

During the Screening period, patients underwent psychiatric and psychological evaluation to rule out current major psychiatric disorders by the administration of the Structured Clinical Interview for Diagnostic and Statistical Manual (DSM) (SCID-I).

Evaluation of Food Craving

The FCQ-T, a self-report inventory, was used to assess food craving. It is a multidimensional questionnaire consisting of 39 items selected from the literature on addiction and eating disorders; it measures nine dimensions of food craving: a) anticipation of positive reinforcement from eating (Ant+); b) anticipation of relief from negative states and feelings from eating (Ant−); c) intentions and plans to consume food (Intent); d) cues that might trigger food cravings (Cues); e) thoughts or worries associated to food (Thoughts); f) craving as hunger (Hunger); g) lack of control over eating (Control); h) emotions that might be experienced before or during food cravings or eating (Emotions); i) guilt from cravings and for giving into them (Guilt).

While total FCQ-T score could be used as a general measure of trait craving, individual FCQ-T factor scores could be useful in identifying and differentiating craving profiles between specific populations. The total score was considered for evaluation in this study. FCQ-T showed a good three-week test-retest reliability, it was, therefore, deemed useful to detect variations of food craving in response to repetitive dTMS effect. FCQ-T was administered at baseline, visit 3, 6, 9, 12, 15, FU1, FU2, and FU3 visits.

Anthropometric Values

Anthropometric measurements were recorded at baseline, at the last dTMS session (visit 15), and at each Follow-up visit (FU1, FU2, and FU3). They included: body weight and height, in order to calculate BMI (kg/m2).

Blood Pressure and Heart Rate

Systolic and diastolic blood pressure (SBP and DBP) were measured using a calibrated device. The device was a mercury sphygmomanometer with a cuff appropriate to the girth of the subject's arm. The same device model was used for each subject throughout the study. Blood pressure was measured under standardized conditions (sitting position), on the same arm. Both SBP and DBP were recorded.

Heart rate (pulse) was measured over one minute under the same conditions for blood pressure, and the results was recorded. Blood pressure and heart rate were measured at each dTMS session (before the TMS treatment and immediately afterwards), and at the FU visits.

Body Composition

The BOD POD (BOD POD® Body Composition System, COSMED, Italy), which uses air displacement plethysmography, was employed to determine body composition and specifically, fat percentage. BOD POD was shown to be as valid as dual energy x-ray absorptiometry. According to standard protocol, subjects were instructed to fast and avoid exercise for at least three hours before the BOD POD measurement. FM and FFM were considered as body composition parameters. Body composition was evaluated at baseline visit, visit 15, and FU2 visit.

Resting Energy Expenditure (REE) and Respiratory Quotient (RQ)

Metabolism analysis was performed by measuring the REE and the RQ. After an overnight fast, REE was measured by indirect calorimetry, using an open-circuit calorimeter (Sensor Medics, Italy). Indirect calorimetry is the reference method for energy expenditure determination. Patients were instructed to limit their physical activity in the evening before the measurement. The REE was assessed continuously during the indirect calorimetry procedure with the subjects laying supine without talking nor sleeping for 30 minutes at a room temperature ranging between 22 and 23° C. The REE measure for each participant considers the mean of the last 25 minutes of the analysis. The RQ was calculated as the ratio between fluxes of released $CO_2$ and consumed $O_2$ derived from the oxidation of the substrates. The value of the RQ depends on what type of substrate (glucose, lipids, or proteins) is being oxidized. Indirect calorimetry was performed at baseline visit, at visit 15, and at FU2 visit.

Activity Energy Expenditure (AEE)

Since baseline visit, participants underwent an evaluation of AEE. Actigraph technology was used to quantify daily calories consumed in relation to physical activity. Actigraph is an accelerometer commonly used in research on physical activity. The raw Actigraph data are converted to counts per minute, which reflect the acceleration and hence, the intensity of physical activity. The higher the counts per minute, the higher the acceleration of the movement measured. The thresholds used to estimate the different intensities of physical activity are determined by validation studies and are predominantly defined in terms of absolute intensity such as METs. Each participant wore an elastic waist belt with the Actigraph accelerometer unit, starting from the baseline visit until the end of the study. The accelerometer was placed over the right hip and it measured acceleration in three different planes of motion: vertical, antero-posterior and medio-lateral. AEE (kcal/day), TEE (kcal/day), average activity time (min/day), average daily steps (steps/day), average daily distance (km/day), very mild physical activity time (min/day), mild physical activity time (min/day), moderate physical activity time (min/day), intensive physical activity time (min/day), and average METs were considered as physical activity parameters. Accelerometer data were analyzed at baseline and at the end of the 5-week treatment period. Data were downloaded to a personal computer using FitMate software (FitMate®, COSMED, Italy).

Laboratory Measurements

Blood tests were carried out before the first dTMS session (T0) and immediately afterwards (T1), before the last dTMS session (T2) and immediately afterwards (T3), and at FU1 and FU2 visits. After a 12-hour overnight fast, a Venflow catheter was placed into an antecubital vein of each participant to draw blood. Blood samples were centrifuged for 15 minutes at 2000 g. A part of the blood was immediately processed; about 10 mL of every sample were stored in aliquots at −80° C. Metabolic, hormonal and neurotransmitter determinations were performed by standardized techniques.

The metabolites assessment included: glucose (mg/dL), fructosamine (μmol/L), glycated hemoglobin (mmol/mol), cholesterol (mg/dL), triglycerides (mg/dL).

The hormonal and neurotransmitter assessment included: insulin (μU/mL), glucagon (pg/mL), leptin (ng/mL), ghrelin (ng/mL), endorphins (ng/mL), epinephrine (pg/mL), norepinephrine (ng/mL), and pituitary hormones [prolactin (ng/mL), ACTH (pg/mL), TSH (μUI/mL), FSH (mUI/mL), LH (mUI/mL)].

Blood sample for catecholamine and pituitary hormones was performed at least 20 minutes after an intravenous cannula was introduced in the antecubital vein, to avoid the conditioning produced by puncture stress. The subjects were also instructed to abstain from several types of food and beverages (e.g. chocolate, licorice, bananas, citrus fruits, coffee, tea, alcohol) for 2-3 days prior to the blood sampling, and from smoking for 10 hours prior to the blood sampling. Catecholamine levels in the blood can change quickly, therefore blood samples were centrifuged and processed within 5 minutes from sampling. Salivary cortisol samples were collected among Hypothalamic-Pituitary-Adrenal (HPA)-axis hormones. Participants chewed on a 3×1 cm inert polymer oral swab (Salivette®, Sarstedt AG & Co., Numbrecht, Germany) for 5 minutes, the swab was then placed into a capped centrifuge tube. Three cortisol (µg/dL) determinations were carried out, one every 15 minutes: before, during and immediately after the dTMS session. Data indicate that cortisol measurement by Salivette® is a reliable prediction method of total and calculated free serum cortisol levels.

Blood glucose was quantified with enzymatic ultraviolet method with hexokinase; serum triglycerides and total cholesterol was determined by the enzymatic colorimetric method. Insulin, prolactin, FSH, LH, ACTH and cortisol were determined with the electrochemiluminescence immunoassay (ECLIA), glucagon with radioimmunoassay (RIA), fructosamine with calorimetric method, and glycated haemoglobin with the turbidimetric inhibition immunoassay (TINIA).

Ghrelin and β-endorphins levels were measured using commercially available enzyme immunoassay (EIA) kits (Phoenix Pharmaceuticals, Burlingame, Calif., USA); enzyme-linked immunosorbent assay (ELISA) kits were used to assess epinephrine, norepinephrine (Elabscience Biotechnology Co. Ltd, Wuhan, China) and leptin (Diagnostic Biochem Canada Inc, London, Ontario, Canada).

Using fasting insulin and glucose levels, HOmeostatic Model Assessment of Insulin Resistance (HOMA-IR) index was computed as follows: fasting insulin (µU/mL)×fasting glucose (mg/dL)/405. HOMA-IR index is frequently used as a valid measure of insulin resistance as it has been proven to be comparable to the euglycemic clamp method.

Results

TMS and Glucose Metabolism Of the 21 patients randomized in the study (5 in group 18+, 5 in group 18−, 3 in group 1+, 3 in group 1−, 5 in the sham group), all were subjected to analysis of glucose metabolism.

In particular, the following parameters were analyzed:
blood glucose, insulin, HOMA-IR: at times T0 (baseline), T1 (after the first rTMS session), T2 (before the last rTMS session), T3 (after the 15th and last rTMS session), FU1 (after 1 month from the end of treatment), FU2 (after 6 months from the end of treatment).
Fructosamine: at times T0, T2, FU1 FU2.

Figure 3:
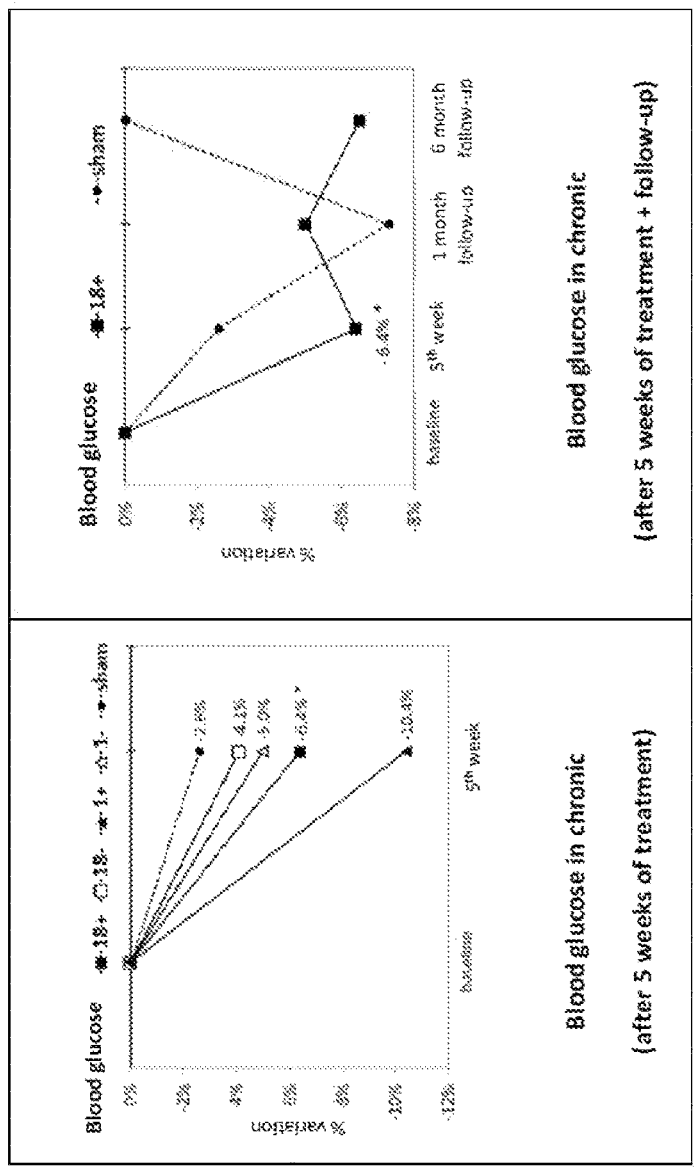
FIGS. 3a, 3b and 3c show the results of the method according to the present invention with reference to the blood glucose values.

FIG. 3a shows the results regarding blood glucose in acute (i.e. after a single session of rTMS). A significant increase was observed in values both in group 18+ (92 mg/dl±11.0 vs 98 mg/dl±12.1 mg/dl, +6.8%±4.4, p=0.027) and in group 18− (82 mg/dl±20.8 vs 91 mg/dl±26.1, +10.3%±8.4, p=0.05).

FIGS. 3b and 3c show the results regarding blood glucose in chronic, comparing the values of blood glucose after the first and after the 15th session of rTMS. A significant reduction was observed in group 18+ (98.2 mg/dl±12.1 vs 94.5 mg/dl±14.2, −6.4%±2.7, p=0.011). In the same group, a tendency towards reduction of blood glucose from baseline was also observed at the follow-up visit conducted 1 month after the end of treatment (in total after 9 weeks: 5 treatment+4 follow-up) (98.2 mg/dl±12.1 vs 95.8 mg/dl±12.0, −5.0%±3.6, p=0.067). At the follow-up done 6 months after the end of treatment, the tendency to a reduction of blood glucose from the baseline in group 18+ continued, though it was not significant (98.2 mg/dl±12.1 vs 96.3 mg/dl±5.5, −6.5%±7.1, p=0.254).

Figure 4:
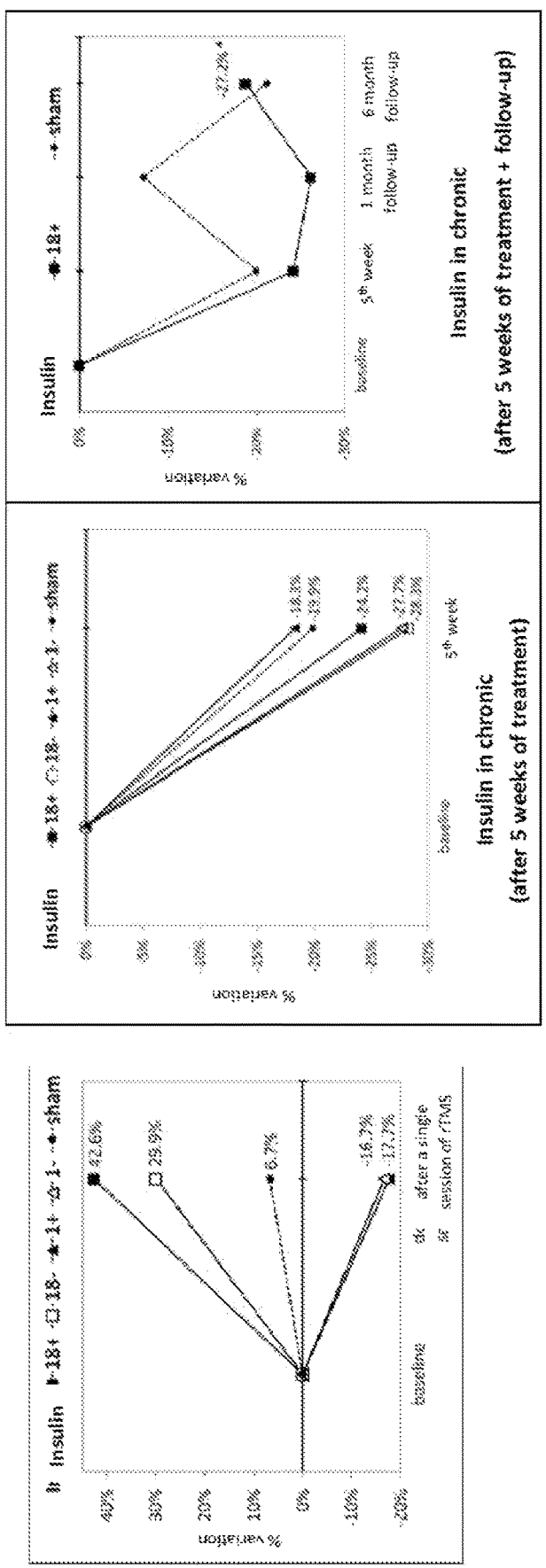
FIGS. 4a, 4b and 4c show the results of the method with reference to the insulin values.

FIG. 4a shows the results regarding insulin in acute. An increase was observed in groups 18+ (+42.6%±97.9) and 18− (+29.9%±23.0), a result not statistically significant, probably due to a wide variability of the insulin values. In group 18−, a tendency to a significant increase in insulin compared to the sham group was observed (+29.9%±23.0 vs +6.7%±13.0, p=0.096). On the contrary, in groups 1+ and 1−, a reduction in insulin levels was observed: −17.7%±20.7 and −16.70±14.5) respectively, although not statistically significant. A tendency to a significant reduction compared to the sham group was observed in group 1− (−16.7%±14.5 vs +6.7%±13.0, p=0.085).

FIGS. 4b and 4c show the results regarding insulin in chronic. After 15 rTMS sessions, a tendency to the reduction in insulin levels was observed in group 18+ (14.3±1.8 vs 10.2±2.15, −24.2±17%, p=0.077). A reduction of insulin levels was also observed in the sham group (19.8±12.5 vs 16.8±13.8, −19.9%±14.1%, p=0.030). However, in group 18+ the reduction of insulin persisted even 6 months after the end of treatment with rTMS (12.9±5.6 vs 10.9±3.9, −27.2±9.2%, p=0.009).

Figure 5:
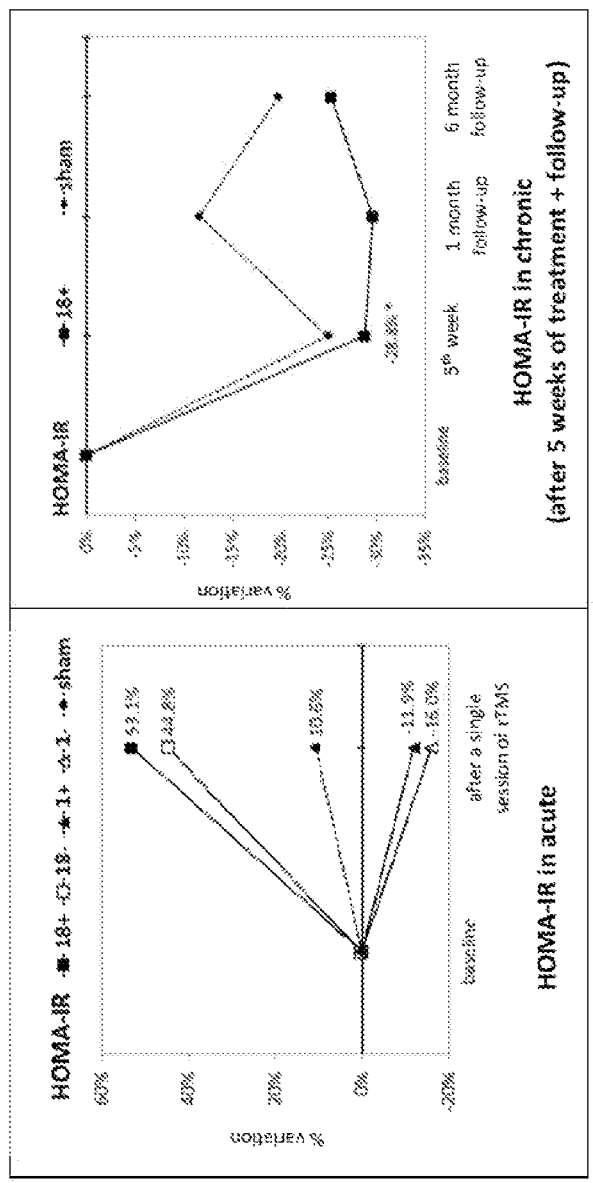
FIGS. 5a, 5b and 5c show the results of the method according to the present invention with reference to the HOMA-IR values.

FIGS. 5a and 5b show the results related to HOMA-IR, respectively, in acute and chronic. In acute, a tendency to the reduction in low frequency treatment groups (1 Hz) and a tendency to increase in those treated at high frequency (18 Hz) was observed, although not significant. These changes reflect those observed in acute for insulin and blood glucose. A tendency of HOMA-IR to significantly increase, in acute, was only observed in the sham group (4.42±2.51 vs 4.86±2.71, +10.6%±10.5, p=0.053).

In chronic, comparing the HOMA-IR values after the first and after the 15th rTMS session, a significant reduction in group 18+ was observed (3.44±0.38 vs 2.43±0.83, −28.8%±17.6, p=0.039). In the same group, the HOMA-IR reduction compared to the baseline persisted at 1 month distance (first follow-up visit) (3.44±0.38 vs 2.41±0.94, −29.6%±22.2, p=0.065) and 6 month distance (second follow-up visit) after treatment with rTMS (3.03±1.51 vs 2.62±1.04, −27.0%±9.8, p=0.084). A reduction trend in chronic of the HOMA-IR was also observed in the sham group (4.86±2.71 vs 3.93±3.18, −25.0%±19.0, p=0.062), but this reduction was no longer detectable at follow-up visits.

The variations of fructosamine were evaluated in chronic. In the 5 groups analyzed, no significant changes in fructosamine values were observed after 15 rTMS sessions or at the follow-up visits.

In order to better investigate the effects of rTMS on glucose metabolism, a differentiated analysis was carried out on patients suffering from type 2 diabetes (blood glucose 126 mg/dl) or impaired fasting glucose (IFG) (blood glucose 110-125 mg/dl), and on non-diabetic patients.

Among the 21 randomized patients, 4 patients with blood glucose anomalies were selected (2 suffering from diabetes mellitus and 2 from IFG; 1 male and 3 females) (DM/IFG) and they were compared with the group of non-diabetic patients (ND) who received the high-frequency treatment (18 Hz). This group was selected as a comparison because it was found to be the one on which rTMS showed the most significant results. Afferent to this group were 8 patients with normal glucose values (2 males and 6 females).

The basal blood glucose values were significantly higher in the group of diabetic/IFG patients compared to healthy ones (123.25±15.11 vs 87.5±5.20, p=0.0001).

Figure 6:
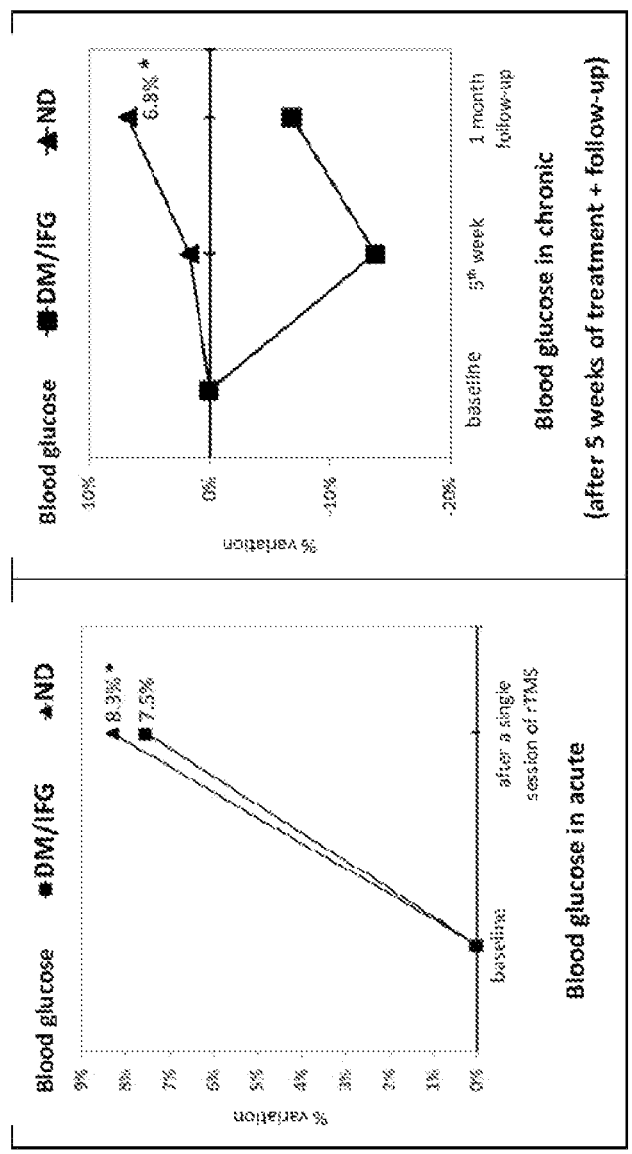
FIGS. 6a and 6b show the results of the method according to the present invention with reference to the blood glucose values in diabetic/IFG and non-diabetic subjects.

FIG. 6a shows the blood glucose values in acute (after a single rTMS session). A significant increase of blood glucose values was observed in the non-diabetic patient group (87.5 mg/dl±5.20 vs 94.0 mg/dl±8.8, +8.3%±7.0, p=0.010), but not in the diabetic/IFG patient group.

As shown in FIG. 6b, in chronic (between the baseline and the 15th rTMS session), no significant changes in blood glucose were observed in non-diabetic patient group. On the contrary, in the group of diabetic/IFG patients, a reduction of blood glucose was observed (123.3 mg/dl±15.1 vs 105.0 mg/dl±4.3, −13.8%±11.7), which tended to be significant compared to the control group of non-diabetic patients (−13.8%±11.7 vs +1.7%±6.9, p=0.069).

This difference between the two groups also persisted at the follow-up visit performed at a distance of one month after the end of treatment (follow-up at 1 month). In fact, while in the diabetic/IFG group blood glucose tended to fall between baseline and follow-up at 1 month (123.3 mg/dl±15.1 vs 106.5 mg/dl±0.7, −6.8%±5.8), a significant increase was observed in the group of non-diabetic patients (87.5 mg/dl±5.2 vs 92.0 mg/dl±11.53, +6.8%±6.2, p=0.028).

Figure 7:
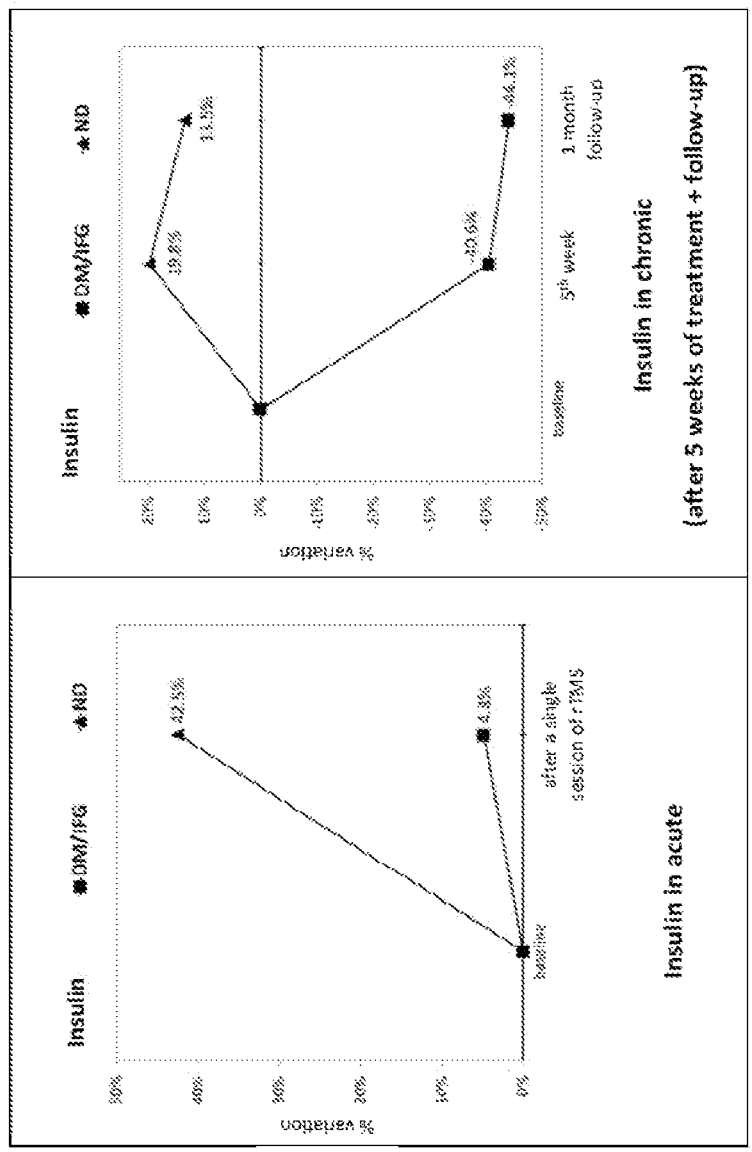
FIGS. 7a and 7b show the results of the method according to the present invention with reference to the insulin values in diabetic/IFG and non-diabetic subjects.

Regarding insulin, in acute (FIG. 7a), a tendency to increase was observed in the group of non-diabetic patients (+42.5%±73, p=0.095), although associated with a considerable variability of the values. As for blood glucose, this change was not observed in the group of diabetic/IFG patients.

In chronic (FIG. 7b), a significant reduction of insulin values was observed in the group of diabetic/IFG patients (52.8 μU/ml±43.7 vs 22.4 μU/ml±9.6, −40.6%±27.8), which was not significant, probably because of the marked variability in insulin values and of the small sample size. However, this change was significant compared to the group of non-diabetic patients (p=0.041).

The same trend of insulin was observed also at a distance of 1 month after the end of treatment with rTMS (between baseline and first follow-up visit) (52.8 μU/ml±43.7 vs 19.6 μU/ml±9.8, −44.1%±25.9).

Figure 8:
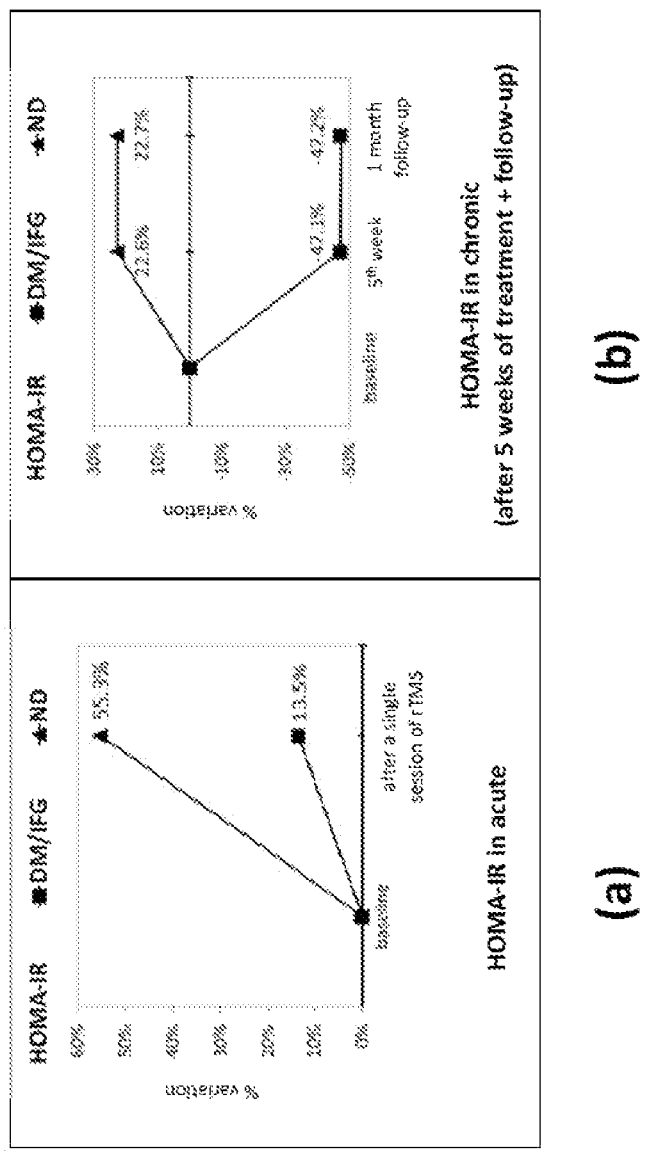
FIGS. 8a and 8b show the results of the method according to the present invention with reference to the HOMA-IR values in diabetic/IFG and non-diabetic subjects.

Regarding the HOMA-IR, it had a trend superimposable to that of insulin (FIG. 8a).

In fact, in acute (after a single rTMS session), a trend to an increase in HOMA-IR was observed in the group of non-diabetic patients (2.62±1.39 vs 3.32±0.31, +55.3%±82.1, p=0.057), although associated with a considerable variability of the values.

In chronic (between the baseline and the 15th rTSM session), a significant reduction of HOMA-IR values was observed in the group of diabetic/IFG patients (17.14±15.85 vs 5.84±2.57, −47.1%±28.2), which was not significant, probably because of the marked variability in insulin values and of the small sample size. However, this change was significant compared to the group of non-diabetic patients (p=0.028).

Such a trend of the HOMA-IR was observed also at a distance of 1 month after the end of treatment with rTMS (between baseline and first follow-up visit) (17.14±15.85 vs 5.16±2.53, −47.2%±27.3). The reduction has a significant trend compared to the non-diabetic patient group (p=0.098).

Comparing the values of HOMA-IR after the first rTMS session and those after 15 sessions, there was a significant reduction of these values also in the non-diabetic patient group (3.32±0.31 vs 2.08±0.52, −23.8%±41, p=0.048).

As for fructosamine, there were no significant differences within groups and between the two groups, perhaps also due to the small sample size of patients with diabetes. However, it is possible to observe a tendency to two different behaviors of fructosamine: in the non-diabetic group, it tends not to vary after 5 weeks of treatment (+1.3%±9.2) and at the 1-month follow-up (+0.4%±9.5) compared to the baseline, whereas in diabetic it tends to decrease, although not significantly, both after 5 weeks of treatment (271.0 umol/L±29.13 vs 247.25 umol/L±34.68, −8.5%±10.8), and at the follow-up (271.0 umol/L±29.13 vs 260.0 umol/L±9.90, −5.7%±5.3).

TMS and Neuroendocrine Structure

All 21 patients randomized in the study were subjected to the analysis of the following neuroendocrine parameters: ghrelin, leptin, beta-endorphins, adrenaline, norepinephrine, ACTH, LH, FSH, GH, TSH, prolactin, cortisol, which were analyzed at times T0, T1, T2, T3, FU1, FU2.

In the 5 groups analyzed, no significant changes in ghrelin values were observed after 15 rTMS sessions or at the follow-up visits.

Figure 9:
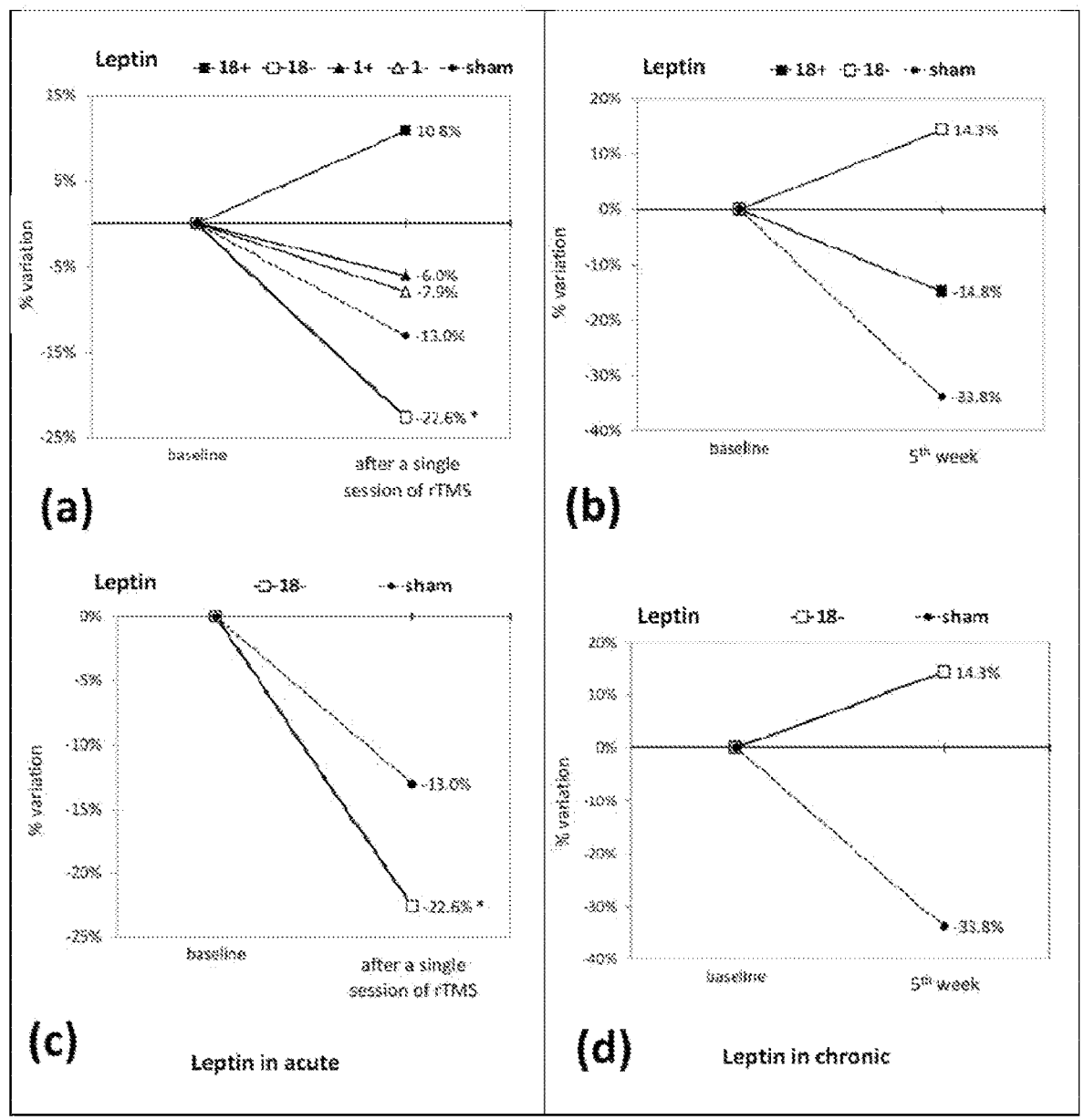
FIGS. 9a, 9b, 9c and 9d show the results of the method according to the present invention with reference to the leptin values.

With regard to leptin, FIGS. 9a and 9c show the results in acute (after a single rTMS session). A significant reduction of its values was observed in group 18− (83.5 ng/ml±51.5 vs 66.5 ng/ml±45.1, −22.6±11.1%, p=0.039). This reduction was also significant compared to that observed in group 1+ (−22.6±11.1% vs −6.0±4.4%, p=0.027).

In chronic (FIGS. 9b and 9d), comparing the values of leptin after the first and after the 15th session of rTMS, a tendency to increase was observed in group 18−, as compared to the other groups (66.5±45.1 vs 75.9±60.1, +14.3±35.5%), which was significant compared to the sham group (p=0.044).

Regarding the changes of adrenaline in acute (i.e. after a single session of rTMS), while a tendency to increasing values was observed in groups 18, although not significantly, in group 1+ there was a significant reduction in the levels of adrenaline (621.2±27.1 vs 558.5±21.9, −10.0±3.3%, p=0.041).

In chronic (between the baseline and the 15th rTMS session), a persistent trend towards lower levels of adrenaline was observed in the groups treated with rTMS at low frequency (1 Hz) which was significant in group 1− compared to the sham group (−36.7±0.7% vs +28±48.5%, p=0.041).

Figure 10:
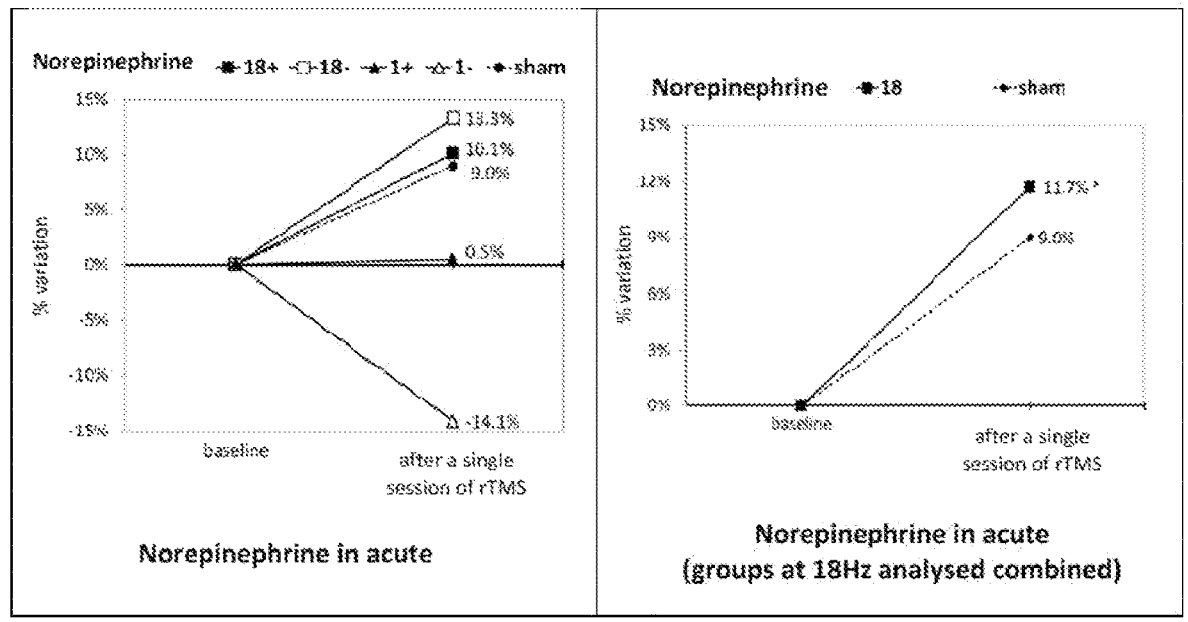
FIGS. 10a, 10b and 10c show the results of the method according to the present invention with reference to the noradrenaline values.
Figure 10:
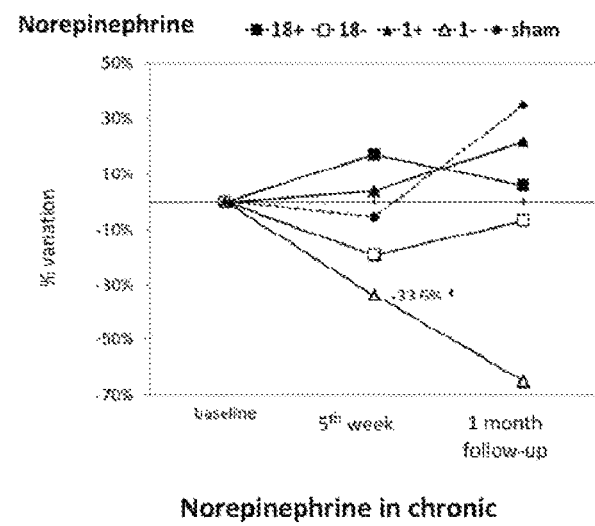

As for adrenaline, in acute (FIGS. 10a and 10b), it was possible to observe a tendency to an increase of the norepinephrine values in the groups treated with rTMS at 18 Hz, although not significant. However, analyzing the combined groups 18+ and 18−, the increase in acute of norepinephrine was significant (70.68±46.09 vs 80.86±56.50, +11.7±23.6%, p=0.05).

In chronic (FIG. 10c), as for adrenaline, a significant reduction in the norepinephrine values was observed in group 1− (65.21±17.70 vs 49.93±6.14, −33.6±2.2%, p=0.012), which was also found to be significant compared to the sham group (−33.6±2.2% vs −5.4±9.4%, p=0.002). In the same group, this reduction persisted even after one month of follow-up, compared to the baseline (65.21±17.70 vs 25.38±1.1, −66.0±4.6%, p=0.071), resulting still significant compared to the sham group (−66.0±4.6% vs +48.4±67.2%, p=0.019).

Figure 11:
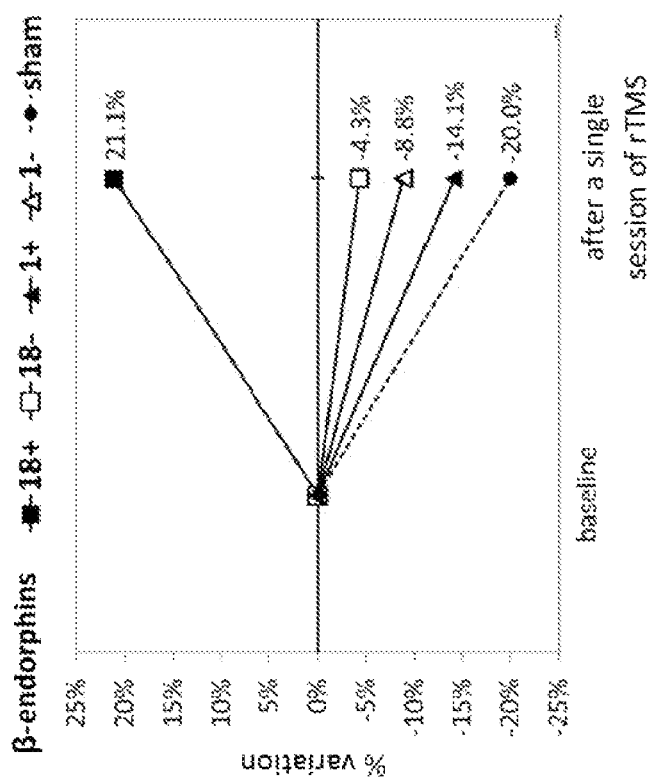
FIG. 11 shows the results of the method according to the present invention with reference to the β-endorphin values.

Regarding β-endorphins, FIG. 11 shows the results in acute (after a single rTMS session). A tendency to an increase of the values was observed in group 18+ (0.27±0.13 vs 0.32±0.13, +21.1±21.1%, p=0.084). This increase was significant both compared to the sham group (p=0.022) and compared to group 1− (p=0.041), in which the values of β-endorphins instead tended to a reduction.

In chronic, β-endorphins were significantly reduced between the baseline and end of treatment, in group 1− (0.47±0.01 vs 0.39±0.02, −19.7±2.6%, p=0.047), and between the baseline and the follow-up visit at a month, in group 1+ (0.20±0.02 vs 0.17±0.03, −18.8±3.4%, p=0.017).

In group 18+, although observing in chronic a tendency to an increase of the β-endorphin values, it was significant compared to the baseline only at the follow-up visit carried out 6 months after the end of treatment with rTMS (0.27±0.13 vs 0.40±0.03, +28.9±1.5%, p=0.018).

No changes were observed either acutely or chronically with regard to: ACTH, FSH, LH and GH.

As regards TSH in acute (after a single rTMS session), a uniform significant reduction was observed in almost all groups: 18+ (−24.7±12.3%, p=0.038), 18− (−24.1±12.8%, p=0.021), 1− (−25.5±10.8%, p=0.089) and sham (−21.5±11.2%, p=0.041). No significant differences were observed between the groups in the TSH change.

In chronic, comparing the values of TSH after the first and after the 15th rTMS session, a tendency to an increase was observed for the values in group 1+ (2.29±1.49 vs 2.85±1.29, +35.3±31.9%, p=0.098), while in group 18+, a tendency to a decrease was observed which was significant only at the follow-up visit one month after the end of treatment (2.96±0.93 vs 2.05±1.09, −34.6±29.2%, p=0.05).

As for TSH, also for prolactin in acute (after a single rTMS session), a uniform significant reduction was observed in almost all groups: 18+ (−45.5%±14.7, p=0.009), 18− (−35.6%±24.2, p=0.043), 1+ (−44.7%±5.0, p=0.017) and sham (−34.5%±6.3, p=0.007). From the comparison between groups, a more significant reduction was observed in group 1+ compared to the sham group (p=0.05).

However, in chronic, a tendency to an increase of prolactin values was observed in the sham group. At the follow-up visit done 1 month after the end of treatment, this increase was significant compared to the baseline (8.04 ng/ml±4.48 vs 11.73 ng/ml±6.56, +45.4%±16.6, p=0.021). At the follow-up visit done 6 months after the end of treatment, compared to baseline, a reduction in the levels of prolactin was observed in groups 18+ (18.28 ng/ml±5.51 vs 12.55 ng/ml±9.91, − 33.50±15.5, p=0.079) and 1+ (15.88 ng/ml±3.73 vs 10.17 ng/ml±0.30, −43.6%±0.3, p=0.008).

Figure 12:
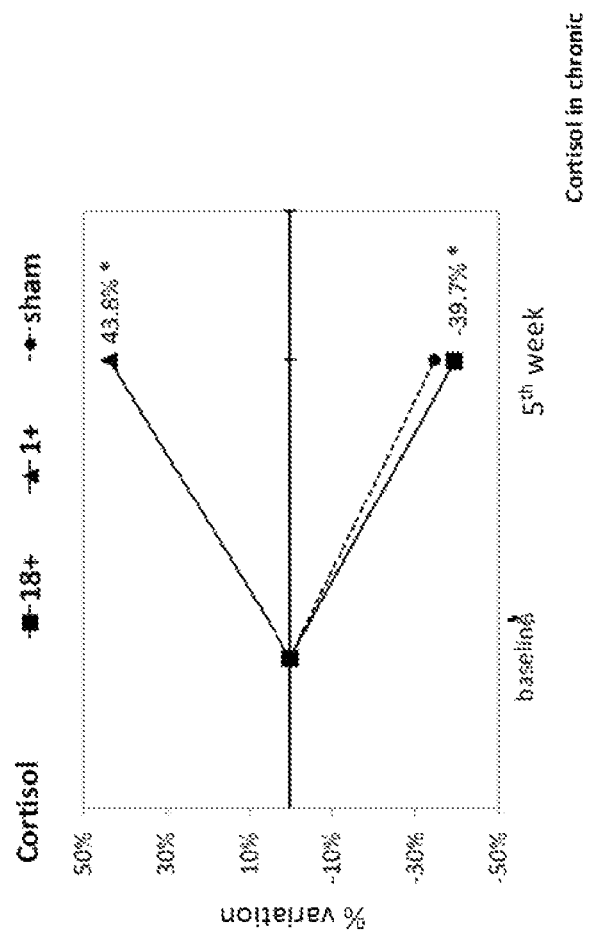
FIG. 12 shows the results of the method according to the present invention with reference to the cortisol values.

FIG. 12 shows the results relating to cortisol. Cortisol was dosed with a triple salivary sampling performed prior to treatment with rTMS, during treatment, and at the end of the same. In the 5 groups analyzed, there were no significant changes of cortisol values in acute.

By comparing the values of cortisol measured at the end of the first treatment with those measured after the 15th treatment session, an opposite tendency was observed in groups 18+ and 1+. While in group 18+, there was a significant reduction in cortisol (0.371 μg/dL±0.198 vs 0.288 μg/dL±0.160, −39.7%±10.6, p=0.026), a significant increase was observed in group 1+ (0.215 μg/dL±0.092 vs 0.297 μg/dL±0.093, +43.8%±24.7, p=0.014).

TMS and Body Temperature

The recording of the body temperature through infrared thermography was performed on 9 out of the 21 randomized patients. The analysis was carried out by dividing patients into 3 groups instead of 5: patients treated with rTMS at 18 Hz (4), patients treated with rTMS at 1 Hz (3), sham-treated patients (2).

Temperature recording was made in 4 times: before and immediately after the first rTMS session, before and immediately after the 15th and last rTMS session.

The body temperature was measured in the abdomen and nail bed of both hands.

The following is an analysis of temperatures recorded at the right index finger nail bed.

The room temperature in all recordings remained constant (23− 24° C.).

Figure 13:
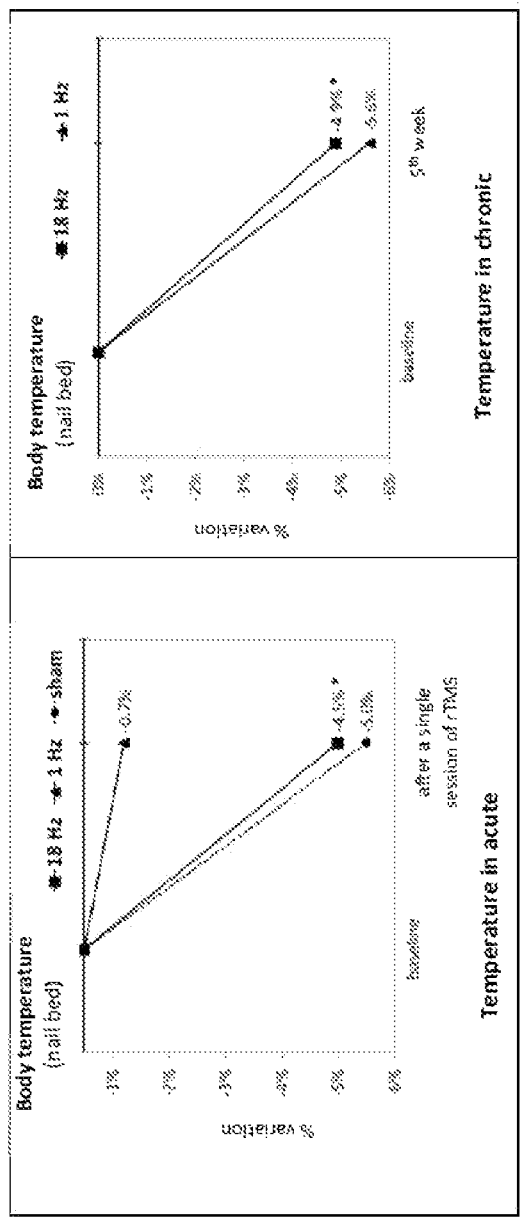
FIGS. 13a and 13b show the results of the method according to the present invention with reference to the body temperature values.

FIG. 13a shows the results in acute, i.e. after the first rTMS session). A significant reduction was observed in the group of patients who received treatment at 18 Hz (34.6° C.±0.9 vs 33.1° C.±1.8, −4.5%±3.0, p=0.05). A reduction in temperature was observed also in the other 2 groups, but not significant.

A similar tendency emerged, in acute, between the first and after the 15th and last session of rTMS: a significant reduction in temperature was observed in the group which received treatment at 18 Hz (34.0° C.±0.7 vs 32.9° C.±1.1, − 3.20±1.7, p=0.033) and a tendency to a decrease in the group which received treatment at 1 Hz (33.7° C.±0.8 vs 32.2° C.±1.6, −4.4%±2.6, p=0.089).

In chronic (FIG. 13b), between the baseline (T0) and the end of the last session of rTMS (T3), a significant reduction of the temperature was observed in the group which received the treatment at 18 Hz (34.6±0.9 vs 32.9±1.1, −4.9±2.7%, p=0.037). No significant changes were observed in the other two groups.

Figure 14:
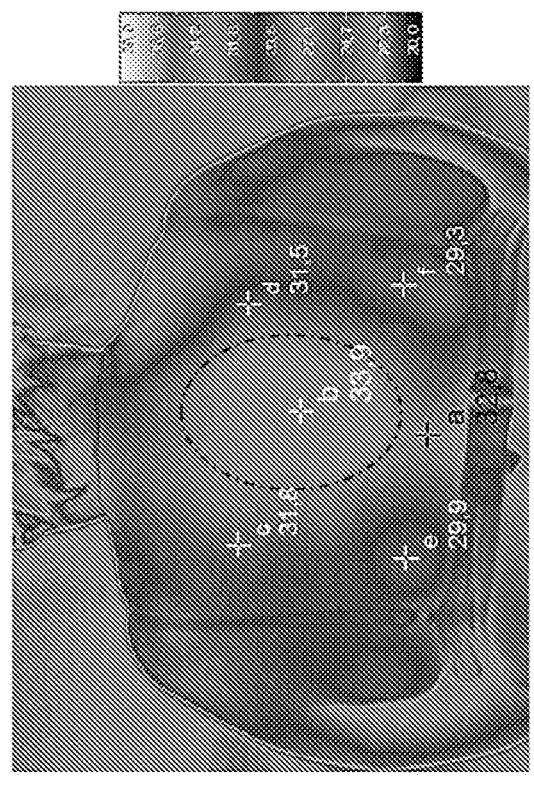
FIGS. 14a and 14b show the thermographic measurement of the interscapular region of an individual before and after a treatment.
Figure 14:
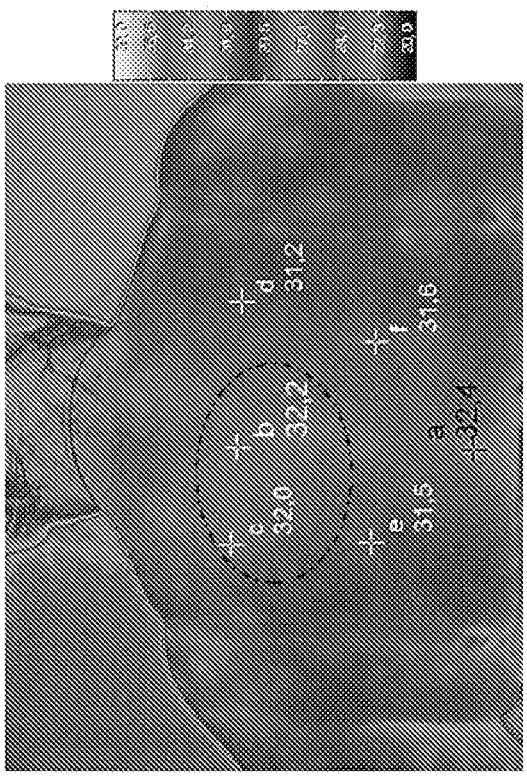
Figure 15:
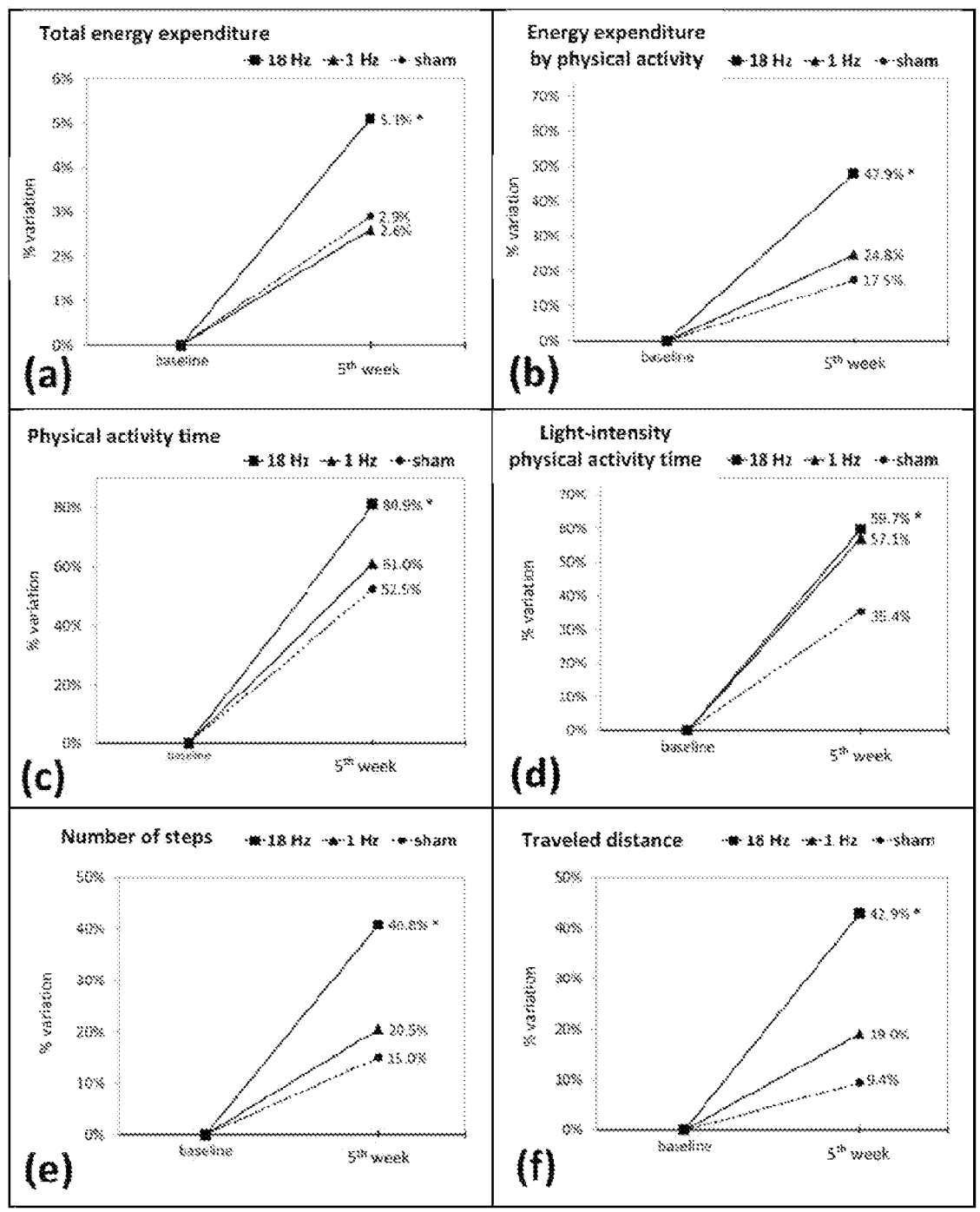
FIGS. 15a, 15b, 15c, 15d, 15e and 15f show the results of the method according to the present invention with reference to the total energy expenditure, the energy expenditure by physical activity, the exercise time, the light intensity physical activity time, the number of steps and the distance covered.

As noted above, in some cases, the patient was subjected to the evaluation of temperature in the interscapular region, where the brown fat resides. FIGS. 14a and 14b show the body temperature in the interscapular region at the baseline (T0), when a BT of about 32.2° C. is measured (FIG. 14a), and after a single dTMS session at high frequency (T1), with a value of about 33.9° C. (FIG. 14b), respectively. Specifically, a selective increase of the individual's skin temperature occurs in the interscapular region of at least 1° C., preferably at least 1.5° C. after repeated application of magnetic stimulation for a treatment of less than 30 minutes, preferably 29.3 minutes. By selective increase in temperature it is meant that the temperature only increases in this area, i.e. the interscapular region, while it does not increase or even decreases in other areas, such as the hands.

TMS and Physical Activity

The physical activity was monitored in 15 out of the 21 randomized patients. However, it was not possible to analyze data obtained from 2 of the 15 patients as they were partial and incomplete, possibly due to an incorrect positioning of the accelerometer, and therefore they were excluded from the analysis. The analysis was, therefore, conducted on a total of 13 patients. As for the body temperature, due to the small sample size, the analysis was conducted by dividing the patients into 3 groups instead of 5:6 treated with rTMS at 18 Hz, 4 treated with rTMS at 1 Hz, 2 treated with sham. The accelerometer was positioned during the screening visit and removed at the last session of rTMS.

Data recording for physical activity was carried out during the screening period and during all 5 weeks of treatment. Data analysis was performed by comparing the parameters of physical activity related to the screening period—1st week of treatment with those of the 5th and last week of treatment. In fact, the FitMate software which processes the accelerometer data analyzes data on a weekly basis, providing a daily average of several parameters, week by week.

Among the parameters taken into account are: Total energy expenditure (Kcal/day), Energy expenditure by activity (Kcal/day), Inactivity time (min/day), Very light-intensity activity (min/day), Light-intensity activity (min/day), Moderate intensity activity (min/day), Intense activity (min/day), METS (average per day), Steps (steps/day), Distance (km/day).

Data analysis showed a significant increase of the following parameters in the group of obese patients who received treatment at high frequency (18 Hz) (FIGS. 15a-15f):

Total energy expenditure (2120.8±338.3 vs 2228.0±361.2, +5.1±5.1%, p=0.046)

Energy expenditure by activity (245.3±129.5 vs 355.7±180.8, +47.9±41.2%, p=0.036)

Activity time (14.7±10.1 vs 24.8±16.8, +80.9±36.1%, p=0.031)

Light-intensity activity (18.7±13.1 vs 27.7±17.1, +59.7±37.4%, p=0.021)

Steps (6098.2±3277.8 vs 8275.5±4253.8, +40.8±37.6%, p=0.028)

Distance in km (4.1±2.4 vs 5.6±3.1, +42.9±44.9%, p=0.044)

A tendency to an increase in the METS average was observed in the same group (1.6±0.3 vs 2.0±0.6, +21.6±18.6%, p=0.069).

No significant changes were observed in the physical activity parameters in the other two treatment groups (1 Hz and Sham), nor significant differences were observed in the comparison between the groups.

Using TMS alone or in combination with insulin or GLP-1 receptor analogs allows a novel treatment of type 2 diabetes both in the early stages (TMS alone) and in the advanced stages (TMS in combination with GLP-1 or insulin analogs).

In particular, two types of treatment can be conceived:
1. Treatment with TMS alone will allow, in the early stages of diabetes, the treatment of the disease through a weight reduction and an increased physical activity. Weight loss and exercise program are the first level of intervention in the treatment of type 2 diabetes according to the joint position statement of ADA-EASD (American society and European society of Diabetology).
2. Treatment with TMS in the advanced stages of the disease may be considered in association with:
    a. GLP-1 analogs (exenatide or liraglutide) with the rationale of increasing the effect of weight control in an additive or even synergistic manner. In fact, TMS acts at the level of the pre-frontal cortex and of the insula by inhibiting the hedonic hunger, while exenatide and liraglutide act at the level of the hypothalamic arcuate nucleus by inhibiting the metabolic hunger.
    b. insulin, which is an excellent pharmacological product for treating type 2 diabetes, except for the negative effect of body weight increase. Therefore, the association of TMS with insulin will be effective in preventing weight gain as a result of insulin therapy.

Deep rTMS proved to be an effective tool in modulating the "reward" dopaminergic circuitry and therefore a possible role of rTMS in controlling the hedonic hunger is conceivable. The preliminary results of a randomized, double-blind, placebo-controlled study showed the efficacy and safety thereof in the treatment of obesity showing, after 15 treatment sessions at high frequency (18 Hz), a significant reduction of food craving and body weight. There was also a role in reducing levels of blood glucose.

However, in order to increase the effectiveness thereof, the combination of two treatments (deep rTMS and GLP-1 receptor agonists) acting synergistically but with different mechanisms of the hedonic and on the homeostatic hunger is conceivable.

For this reason, a randomized clinical open trial was designed to compare the efficacy and safety of deep rTMS and of the GLP-1 receptor agonists (exenatide and liraglutide) as well as their association in the food craving and body weight control, in a population of obese subjects. Given the role of both treatments in modulating blood glucose and insulin secretion, the effects on glucose and on the neuro-endocrine structure will be evaluated and compared. In particular, 5 treatment groups will be compared: rTMS, Liraglutide, Exenatide, rTMS+Liraglutide, rTMS+Exenatide, for a period of 8 weeks.

TMS and Microbiota

Figure 16:
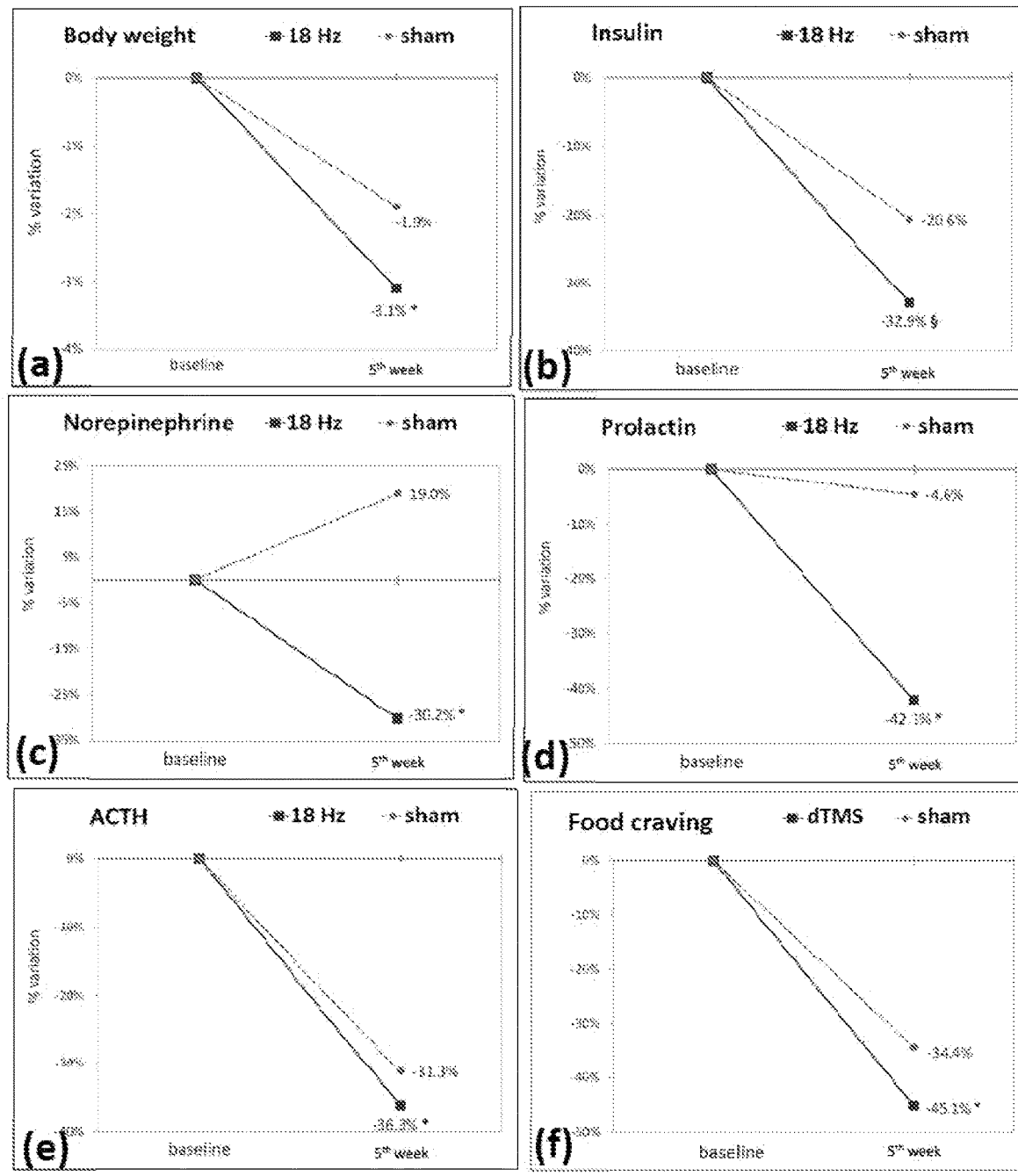
FIGS. 16a, 16b, 16c, 16d, 16e and 16f show the results of the method according to the present invention with reference to the intestinal microbiota analysis.

FIGS. 16a and 16b show how after five weeks there is a significant reduction of body weight (−3.1±2.6%; P<0.01) and of the fat mass (in Kg) (−4.2±6%; P<0.05) for the TMS group. In particular, there was a significant decrease in insulin levels compared to the sham group (−32.9±31.1%; P<0.05). In the same group of subjects there was a significant reduction of TSH (2.8±1.4 vs 2.0±0.9 μUI/ml; −15.6±20%; P<0.05), of prolactin (15.8±4.2 vs 9.2±2.6 ng/ml; −42.1±3.9%; P<0.01), ACTH (30.2±6.4 vs 18.0±6.8 μg/ml; −36.3±26.8%; P<0.01) and norepinephrine level (46.7±24.2 vs 28.9±6.9 ng/ml; −30.2±34.4%; P<0.05), as shown in FIGS. 16c, 16d and 16e.

FIG. 16f shows a significant reduction of food craving as a result of MS treatment (−45.1%±14.6 vs baseline, P<0.001).

Figure 17:
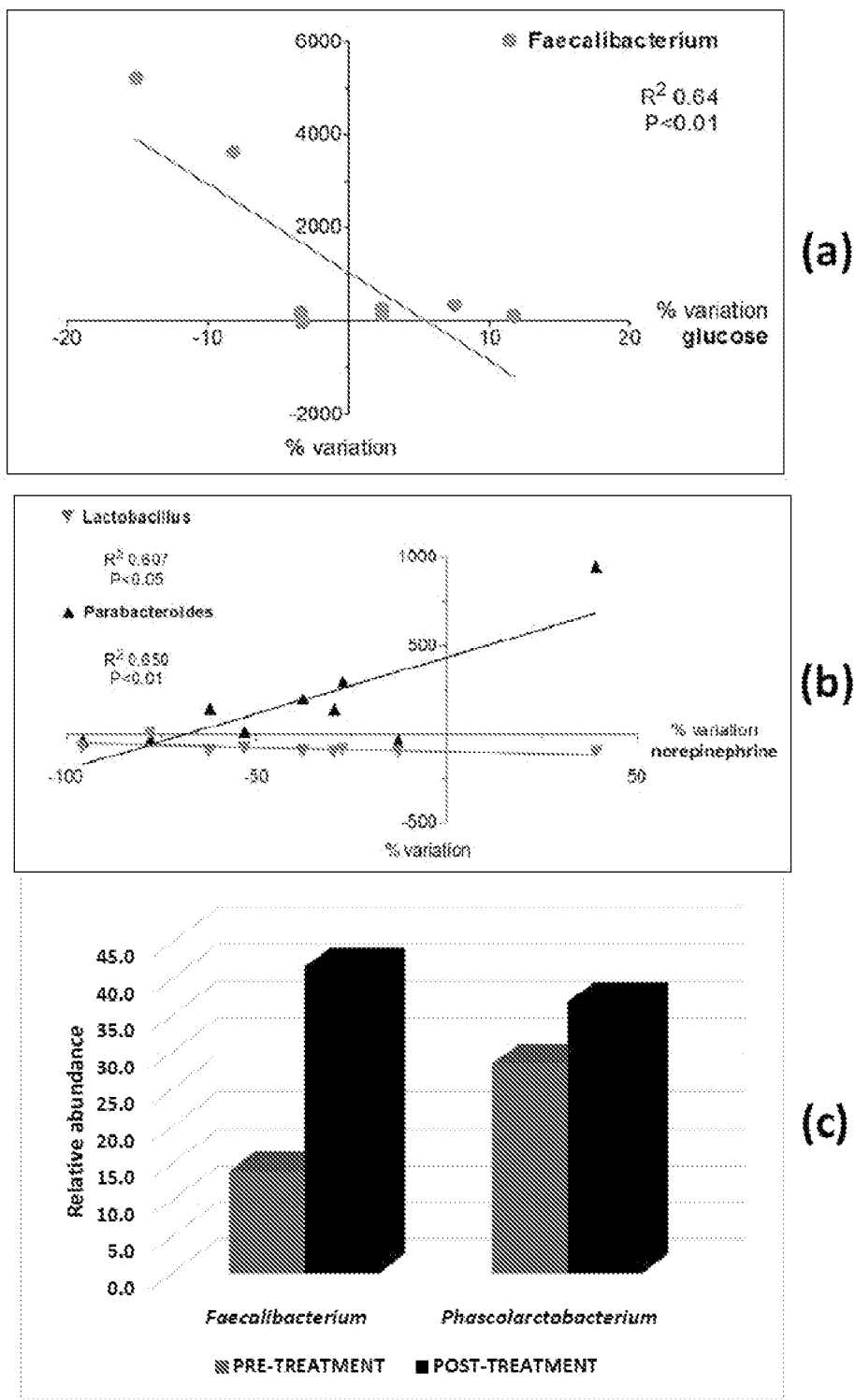
FIGS. 17a, 17b and 17c show the results of the method according to the present invention with reference to the values of *Faecalibacterium* and Parabacteroides.

FIGS. 17a, 17b and 17c show how TMS significantly increases the abundance of *Faecalibacterium* and Phascolarctobacterium with respect to the starting samples with an increase of 66% and 23%, respectively. In addition, there is an inverse correlation between the increase in the percentage of glucose reduction and *Faecalibacterium* (R2: 0.642; P<0.01). In the group treated with TMS, norepinephrine varies significantly correlated with the decrease of *lactobacillus* (R2: 0607; P<0.05) (more abundant in obese patients) and with the increase of the anti-inflammatory bacterium Parabacteroides (R2: 0.650; P<0.01).

Figure 18:
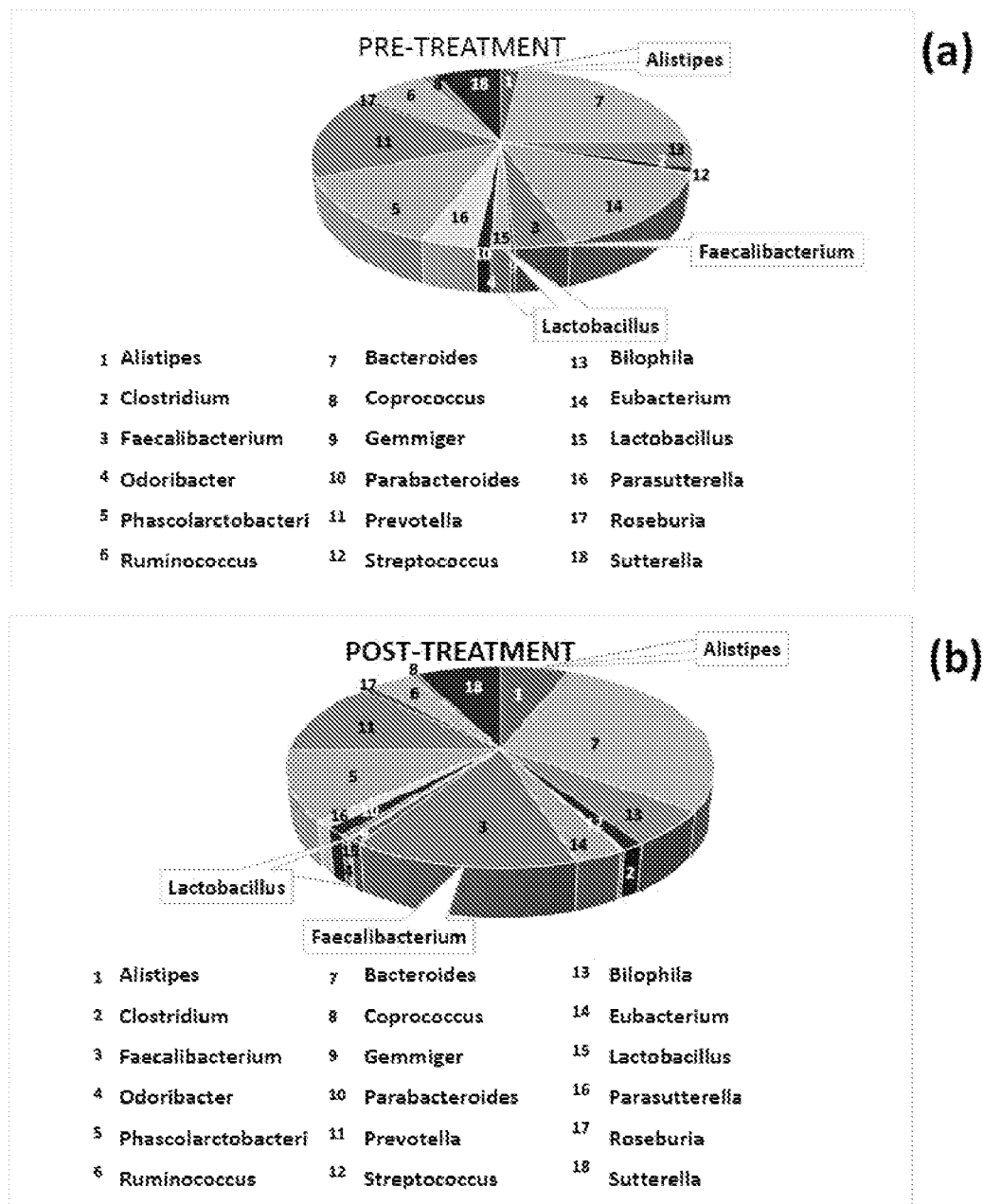
FIGS. 18a and 18b show the composition of the intestinal microbiota before and after treatment for the high frequency TMS group.
Figure 19:
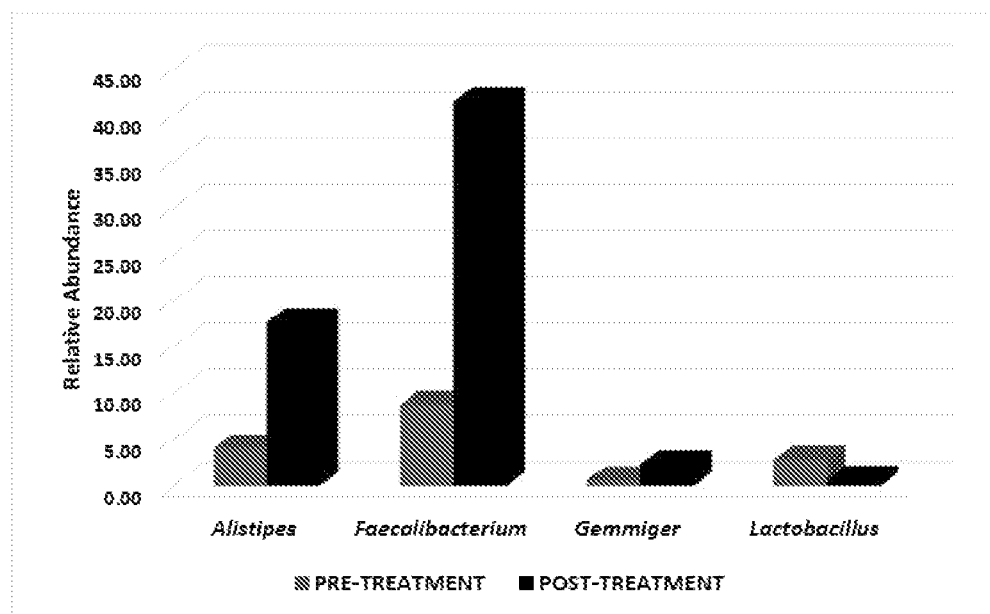
FIG. 19 shows the change of some significant parameters with reference to FIGS. 18a and 18b.

FIGS. 18a and 18b show the composition of the intestinal microbiota before and after treatment in the case of the high frequency TMS group. FIG. 19 instead shows a detail of the variation of some bacteria. After five weeks of treatment, a significant increase is observed in *Faecalibacterium* (p=0.014) and Alistipe (p=0.032) and a significant decrease of *Lactobacillus* (p=0.030) with respect to the reference base group.

Figure 24:
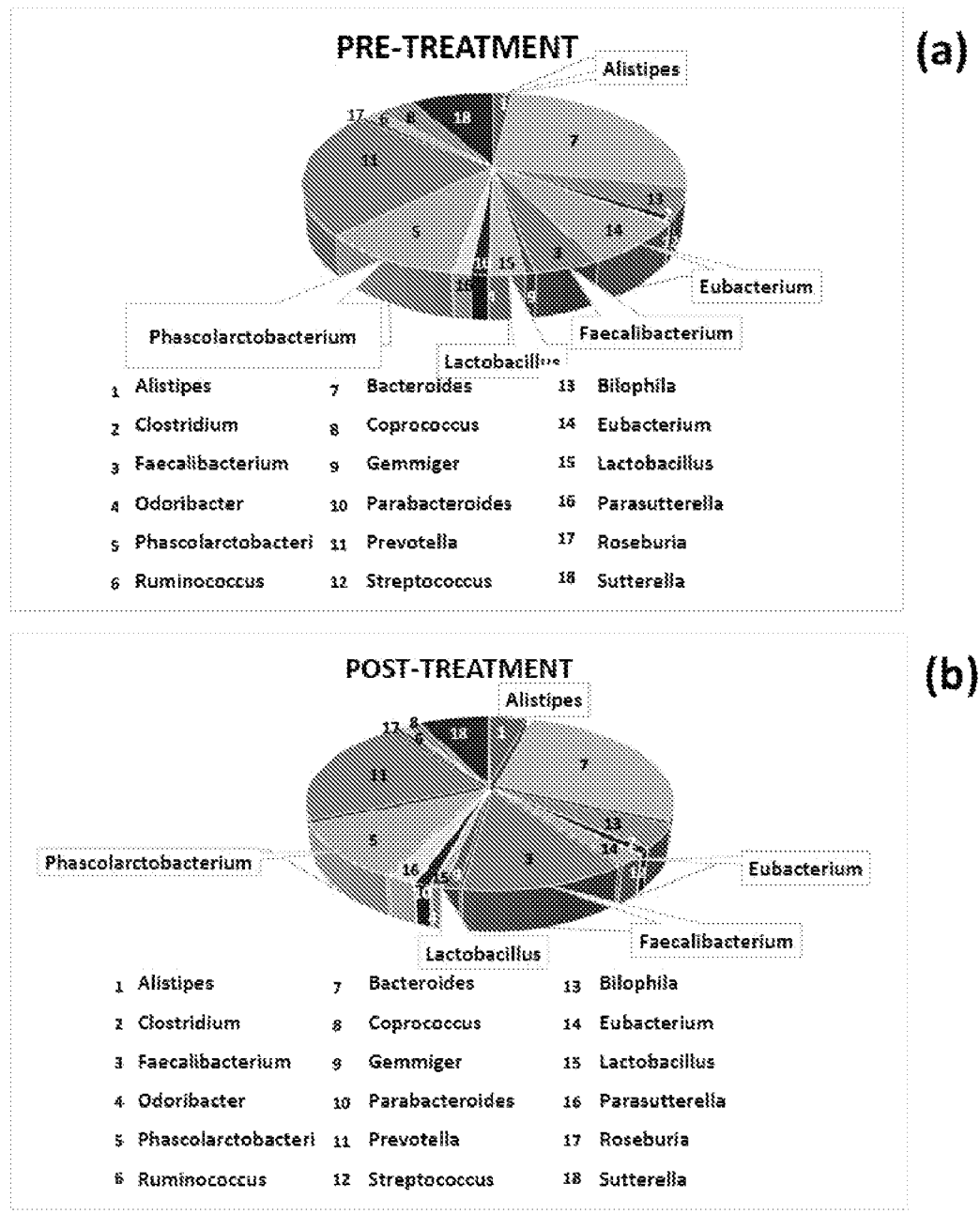
FIGS. 24a and 24b show the composition of the intestinal microbiota before and after treatment for the low frequency TMS group.
Figure 25:
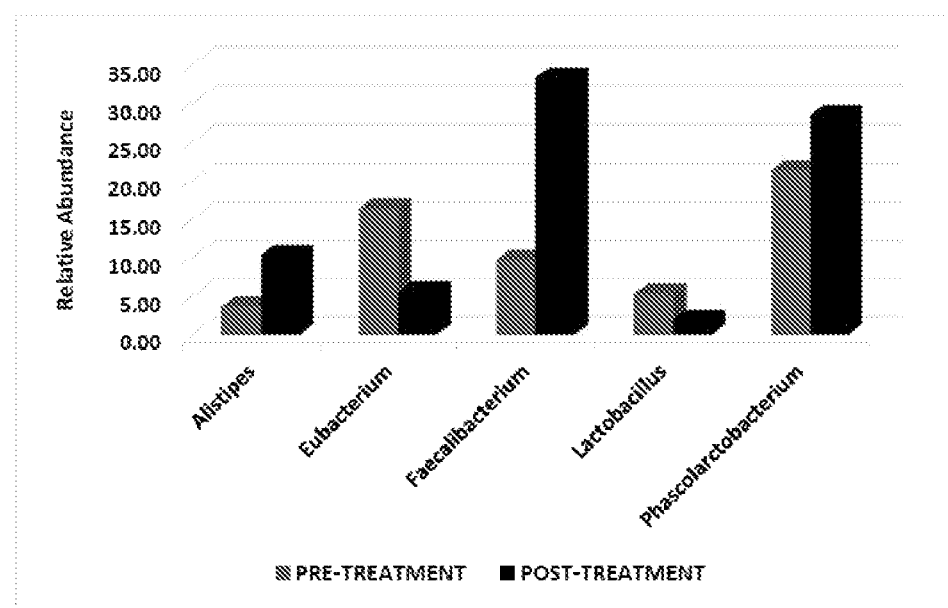
FIG. 25 shows the change of some significant parameters with reference to FIGS. 24a and 24b.

FIGS. 24a and 24b show the composition of the intestinal microbiota before and after treatment in the case of the low frequency TMS group. FIG. 25 instead shows a detail of the variation of some bacteria. After five weeks of treatment, a significant increase is observed in *Faecalibacterium* (p=0.020) and Alistipe ((p=0.003) of Parasutterella (p=0.001) and Phascolarctobacterium (p=0.016) and a significant decrease of *Eubacterium* (p=0.0002) with respect to the reference base group.

Figure 26:
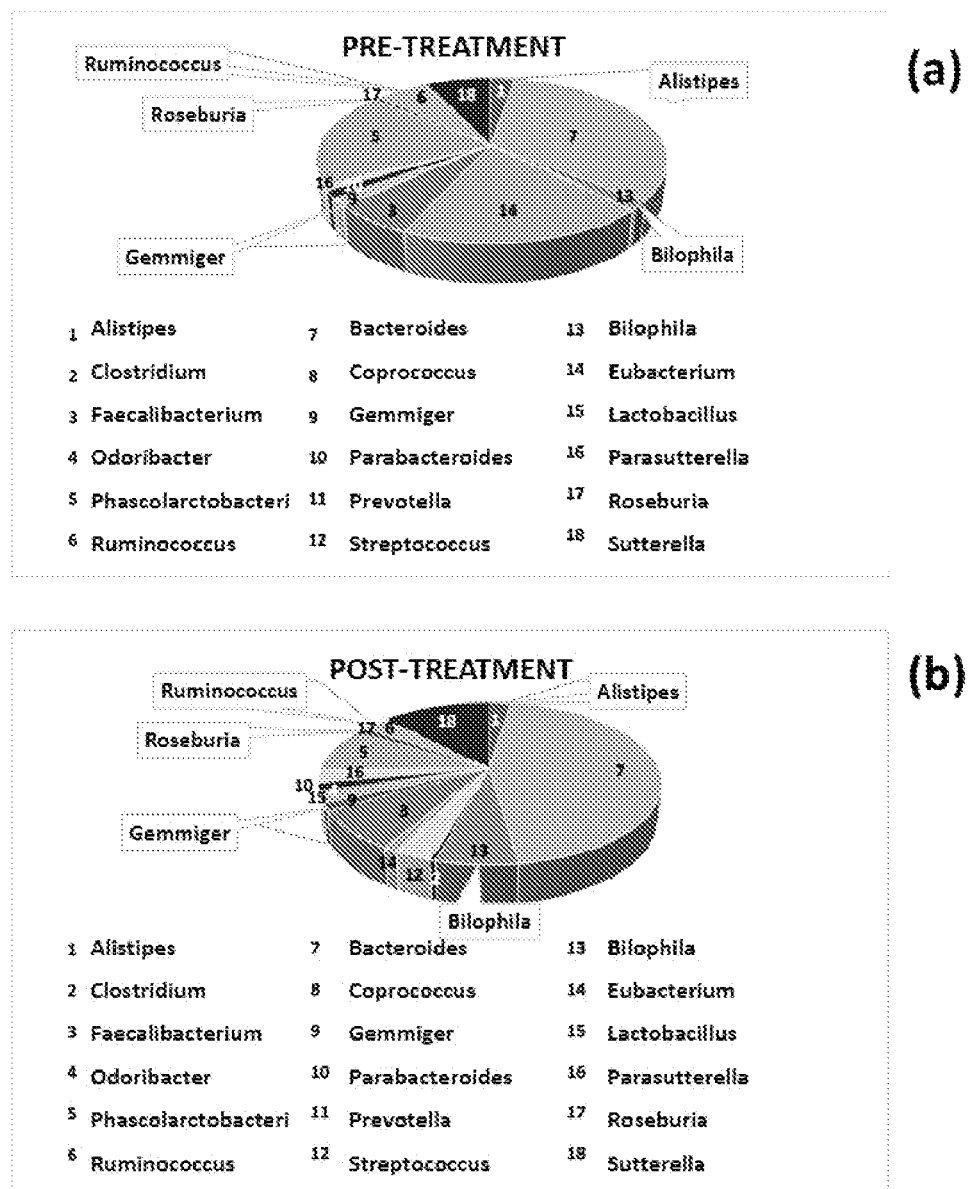
FIGS. 26a and 26b show the composition of the intestinal microbiota before and after treatment for the sham group.
Figure 27:
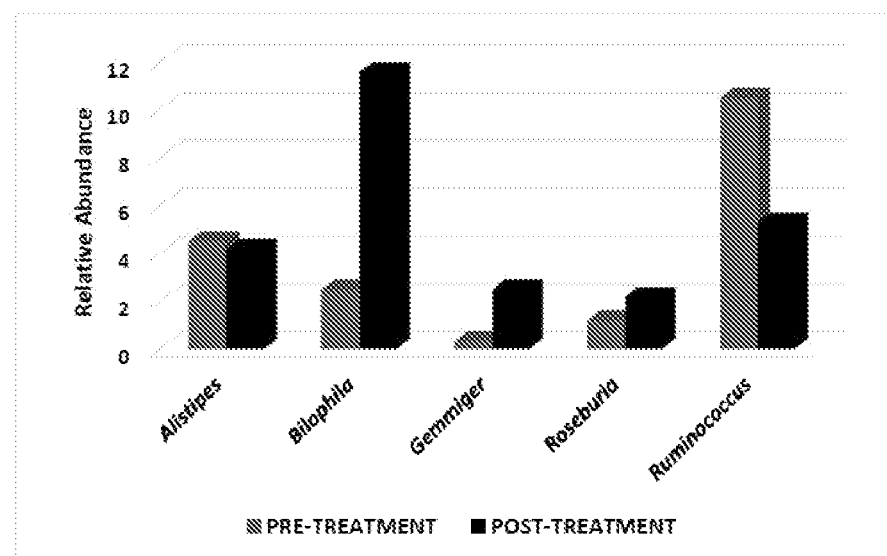
FIG. 27 shows the change of some significant parameters with reference to FIGS. 26a and 26b.

FIGS. 26a and 26b show the composition of the intestinal microbiota before and after treatment in the case of the sham (placebo) group. FIG. 27 instead shows a detail of the variation of some bacteria. After five weeks of treatment, a significant increase is observed in Bilophila (p=0.014), Gemmiger (p=0.021) and *Roseburia* (p=0.024) and a significant decrease of Alistipes (p=0.0037) and Ruminococcus (p=0.001) with respect to the reference base group.

Figure 28:
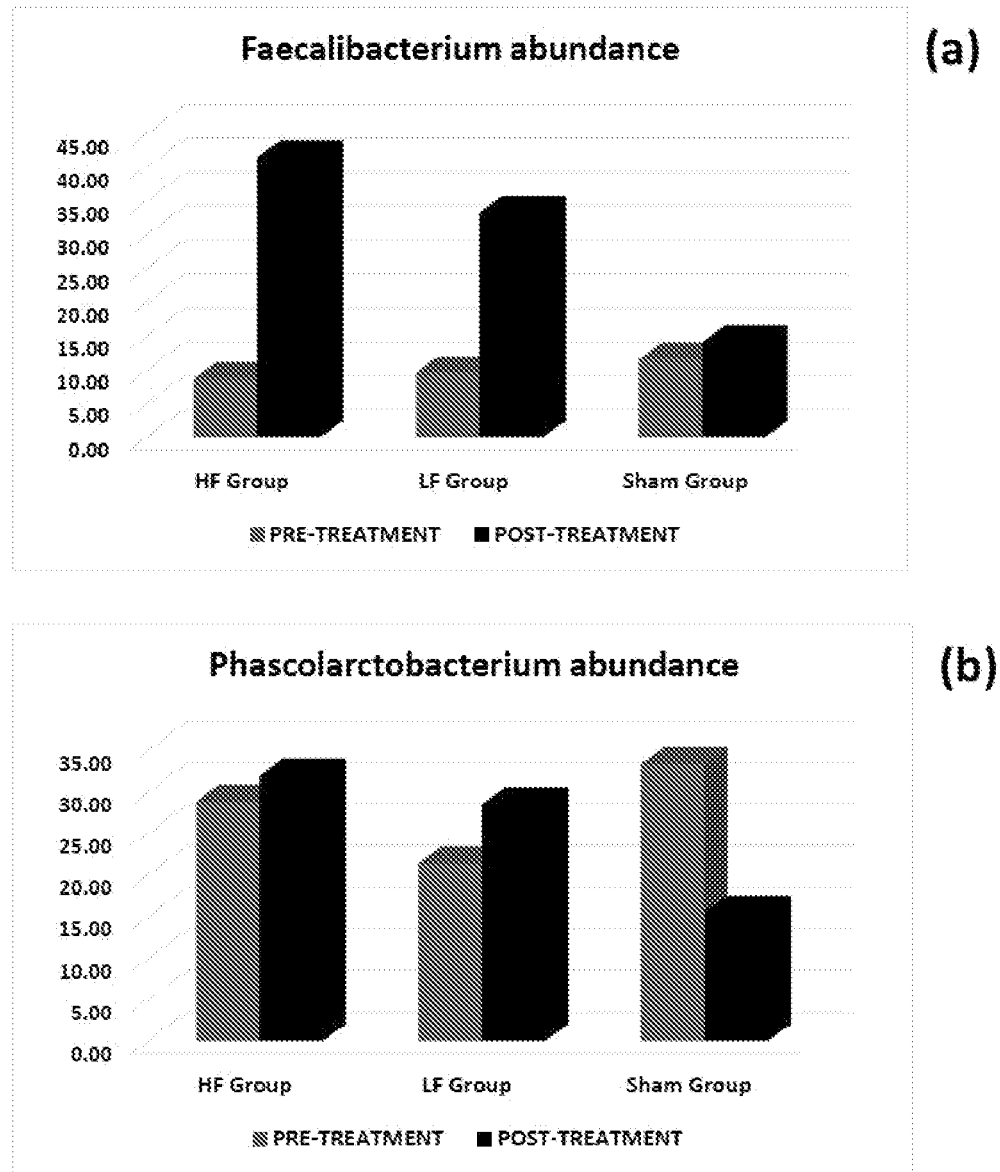
FIGS. 28a and 28b show the variation of the *Faecalibacterium* and phascolarctobacterium bacteria before and after treatment for the high frequency, low frequency and placebo groups.

FIGS. 28a and 28b show how the *Faecalibacterium* always increases after treatment and significantly after high frequency treatment while Phascolactobacterium increases only in the case of high and low frequency treatment, while it decreases in the case of sham.

TMS and Food Craving

Food Craving

Figure 20:
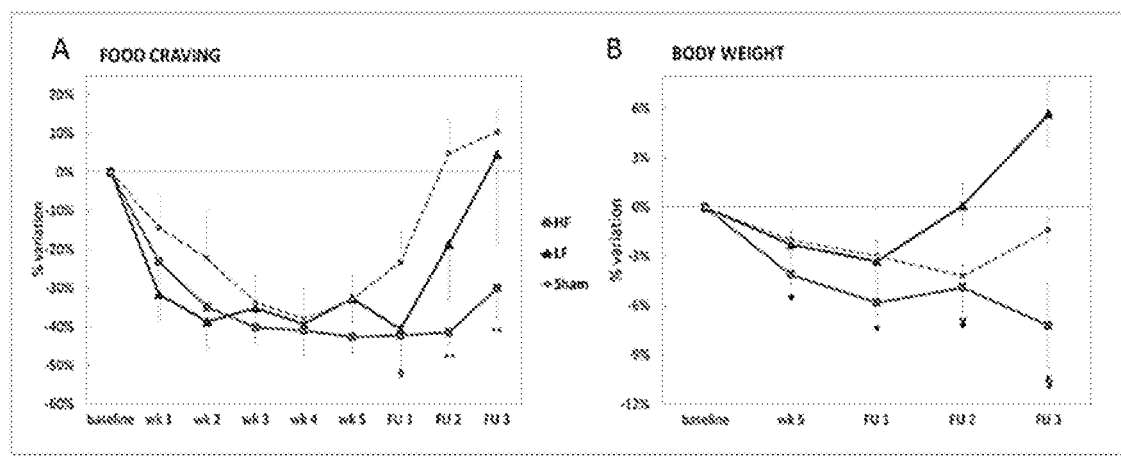
FIGS. 20a and 20b show the treatment effects on hedonic hunger and body weight.

The variations in food craving (evaluated by FCQ-T score) among the groups are presented in Table 5 and FIG. 20A.

After 15 dTMS sessions, a significant decline in food craving was noticed in all groups (HF: $-42.7\pm4.1\%$ vs baseline, p=0.000001; LF: $-32.7\pm6.0\%$ vs baseline, p=0.004; Sham: $-32.9\pm6.7\%$ vs baseline, p=0.006). No significant difference in craving decrease were found between groups.

Comparing food craving variation after 5 weeks of treatment between the two sub-groups HF (cue) and HF (no cue), a trend to a higher reduction was found in the HF (cue) ($-49.4\pm5.9\%$ vs $-35.0\pm4.7\%$, p=0.076), which tended to be significant also compared to Sham ($-49.4\pm5.9\%$ vs $-32.9\pm6.7\%$, p=0.084).

The food craving reduction continued even after 4 weeks of follow-up (FU1) in HF ($-42.3\pm4.0\%$ vs baseline, p=0.000004), in LF ($-40.7\pm9.3\%$ vs baseline, p=0.012) and in Sham ($-23.2\pm8.1\%$ vs baseline, p=0.040). At FU1, pairwise analysis revealed a trend to higher reduction of food craving in HF compared to Sham (p=0.063).

After 6 months of follow-up (FU2), food craving significantly continued to decrease in HF only ($-41.5\pm3.1\%$ vs baseline, p=0.000004). At FU2, pairwise analysis revealed a significant difference in the variation of food craving between HF and Sham (p=0.004).

A re-evaluation of food craving was performed 1 year after the end of treatment (FU3) in 14 of the 33 enrolled patients (HF n=8; LF n=2; Sham n=4): a significant decrease in food craving was found in HF ($-30.1\pm8.0\%$, p=0.009 vs baseline; p=0.002 vs Sham), whilst a trend to increase was observed in LF and Sham.

TABLE 4

More significant acute and chronic variations of measured parameters

| | T0 | T1 | T0 vs T1 | T2 | T0 vs T2 | HF vs Sham | HF vs LF | LF vs Sham | |
|---|---|---|---|---|---|---|---|---|---|
| Weight (kg) | | | | | | p < 0.05 | p = 0.087 | p = 0.759 | C |
| HF | 101.4 ± 4.7 | — | — | 97.3 ± 4.4 | p < 0.0001 | | | | |
| LF | 101.3 ± 6.0 | — | — | 99.1 ± 6.0 | p < 0.05 | | | | |
| Sham | 96.3 ± 3.5 | — | — | 94.5 ± 3.8 | p < 0.05 | | | | |
| BMI (kg/m$^2$) | | | | | | p < 0.05 | p = 0.084 | p = 0.913 | C |
| HF | 36.4 ± 1.3 | — | — | 35.0 ± 1.2 | p < 0.0001 | | | | |
| LF | 37.5 ± 2.1 | — | — | 36.8 ± 2.1 | p < 0.05 | | | | |
| Sham | 35.7 ± 0.9 | — | — | 35.0 ± 1.0 | p < 0.01 | | | | |
| REE (%) | | | | | | p = 0.493 | p = 0.905 | p = 0.450 | C |
| HF | 93.6 ± 3.1 | — | — | 85.6 ± 2.2 | p < 0.05 | | | | |
| LF | 94.4 ± 4.2 | — | — | 85.9 ± 2.6 | p = 0.073 | | | | |
| Sham | 93.3 ± 3.9 | — | — | 89.1 ± 3.1 | p = 0.256 | | | | |
| RQ | | | | | | p = 0.204 | p = 0.243 | p = 0.055 | C |
| HF | 0.86 ± 0.01 | — | — | 0.82 ± 0.01 | p < 0.05 | | | | |
| LF | 0.88 ± 0.02 | — | — | 0.82 ± 0.01 | p < 0.05 | | | | |
| Sham | 0.86 ± 0.02 | — | — | 0.87 ± 0.03 | p = 0.754 | | | | |
| Heart rate (pulses/min) | | | | | | p = 0.557 / p = 0.917 | p = 0.529 / p = 0.829 | p = 0.859 / p = 0.936 | A / C |
| HF | 82.6 ± 2.3 | 73.0 ± 1.6 | p < 0.01 | 73.8 ± 1.7 | p = 0.466 | | | | |
| LF | 82.7 ± 3.1 | 78.2 ± 3.2 | p = 0.112 | 76.1 ± 2.7 | p = 0.178 | | | | |
| Sham | 78.2 ± 2.6 | 76.0 ± 2.3 | p = 0.344 | 75.3 ± 3.5 | p = 0.487 | | | | |
| TEE (kcal/day) | | | | | | p = 0.157 | p = 0.942 | p = 0.156 | C |
| HF | 2188.5 ± 106.1 | — | — | 2296.4 ± 119.6 | p < 0.05 | | | | |
| LF | 2100.8 ± 58.2 | — | — | 2198.2 ± 63.6 | p = 0.052 | | | | |
| Sham | 1874.0 ± 50.8 | — | — | 1881.8 ± 63.1 | p = 0.842 | | | | |
| AEE (kcal/day) | | | | | | p = 0.070 | p = 0.840 | p = 0.156 | C |
| HF | 216.0 ± 29.5 | — | — | 326.0 ± 55.1 | p < 0.05 | | | | |
| LF | 238.5 ± 38.9 | — | — | 324.3 ± 35.0 | p = 0.089 | | | | |
| Sham | 255.4 ± 47.6 | — | — | 263.2 ± 50.1 | p = 0.842 | | | | |
| METs | | | | | | p = 0.080 | p = 0.955 | p = 0.428 | C |
| HF | 1.6 ± 0.1 | — | — | 1.9 ± 0.2 | p < 0.05 | | | | |
| LF | 1.6 ± 0.2 | — | — | 1.8 ± 0.1 | p = 0.423 | | | | |
| Sham | 1.7 ± 0.2 | — | — | 1.8 ± 0.1 | p = 0.426 | | | | |
| Kilometers (km/day) | | | | | | p = 0.069 | p = 0.705 | p = 0.150 | C |
| HF | 3.4 ± 0.5 | — | — | 4.9 ± 0.9 | p = 0.073 | | | | |
| LF | 3.8 ± 0.7 | — | — | 4.8 ± 0.6 | p = 0.127 | | | | |
| Sham | 4.5 ± 0.9 | — | — | 4.5 ± 0.8 | p = 0.923 | | | | |
| Glucose (mg/dL) | | | | | | p < 0.05 / p = 0.860 | p = 0.190 / p = 0.449 | p = 0.575 / p = 0.680 | A / C |

TABLE 4-continued

More significant acute and chronic variations of measured parameters

| | T0 | T1 | T0 vs T1 | T2 | T0 vs T2 | HF vs Sham | HF vs LF | LF vs Sham | |
|---|---|---|---|---|---|---|---|---|---|
| HF | 87.9 ± 4.3 | 95.0 ± 4.6 | p < 0.001 | 85.6 ± 2.9 | p = 0.265 | | | | |
| LF | 103.6 ± 11.3 | 107.8 ± 11.4 | p = 0.128 | 95.6 ± 8.8 | p = 0.150 | | | | |
| Sham | 94.7 ± 6.0 | 99.4 ± 12.5 | p = 0.607 | 93.1 ± 3.1 | p = 0.554 | | | | |
| Insulin (μU/mL) | | | | | | p = 0.166 | p = 0.074 | p = 0.415 | A |
| | | | | | | p = 0.780 | p = 0.314 | p = 0.424 | C |
| HF | 20.1 ± 5.2 | 20.5 ± 6.0 | p = 0.894 | 12.3 ± 1.9 | p = 0.086 | | | | |
| LF | 30.8 ± 9.8 | 27.5 ± 9.7 | p = 0.073 | 19.1 ± 3.0 | p = 0.194 | | | | |
| Sham | 19.5 ± 5.1 | 18.6 ± 4.6 | p = 0.437 | 15.7 ± 2.6 | p = 0.270 | | | | |
| HOMA-IR | | | | | | p = 0.128 | p = 0.071 | p = 0.508 | A |
| | | | | | | p = 0.823 | p = 0.241 | p = 0.307 | C |
| HF | 4.9 ± 1.5 | — | — | 2.7 ± 0.5 | p = 0.074 | | | | |
| LF | 8.9 ± 3.7 | — | — | 5.1 ± 1.2 | p = 0.261 | | | | |
| Sham | 4.6 ± 1.3 | — | — | 3.6 ± 0.6 | p = 0.167 | | | | |
| Glycated hemoglobin (mmol/mol) | | | | | | p = 0.518 | p = 0.075 | p = 0.271 | C |
| HF | 36.3 ± 4.8 | — | — | 33.1 ± 4.4 | p < 0.01 | | | | |
| LF | 41.0 ± 8.4 | — | — | 40.0 ± 7.8 | p = 0.650 | | | | |
| Sham | 34.8 ± 6.2 | — | — | 33.3 ± 6.1 | p = 0.321 | | | | |
| Leptin (ng/mL) | | | | | | p = 0.638 | p = 0.066 | p = 0.144 | A |
| | | | | | | p = 0.419 | p = 0.392 | p = 0.683 | C |
| HF | 66.9 ± 10.3 | 56.3 ± 9.0 | p < 0.01 | 48.4 ± 12.7 | p = 0.062 | | | | |
| LF | 80.7 ± 17.3 | 74.4 ± 15.4 | p = 0.130 | 61.0 ± 11.5 | p = 0.116 | | | | |
| Sham | 104.2 ± 39.5 | 102.2 ± 35.6 | p < 0.05 | 65.1 ± 18.9 | p = 0.247 | | | | |
| Norepinephrine (ng/mL) | | | | | | p = 0.726 | p = 0.064 | p = 0.357 | A |
| | | | | | | p = 0.295 | p = 0.671 | p = 0.150 | C |
| HF | 5.4 ± 1.1 | 5.7 ± 1.5 | p < 0.05 | 4.4 ± 1.3 | p = 0.377 | | | | |
| LF | 5.3 ± 0.7 | 4.8 ± 0.9 | p = 0.787 | 4.3 ± 0.8 | p = 0.173 | | | | |
| Sham | 5.0 ± 1.0 | 4.4 ± 1.2 | p = 0.536 | 4.4 ± 1.4 | p = 0.302 | | | | |
| β-Endorphin (ng/mL) | | | | | | p < 0.05 | p < 0.05 | p = 0.505 | A |
| | | | | | | p = 0.994 | p = 0.257 | p = 0.490 | C |
| HF | 0.299 ± 0.05 | 0.328 ± 0.05 | p < 0.05 | 0.302 ± 0.05 | p = 0.943 | | | | |
| LF | 0.424 ± 0.06 | 0.392 ± 0.06 | p = 0.180 | 0.386 ± 0.05 | p = 0.128 | | | | |
| Sham | 0.366 ± 0.07 | 0.297 ± 0.06 | p = 0.289 | 0.367 ± 0.07 | p = 0.976 | | | | |
| Cortisol (μg/dL) | | | | | | p = 0.247 | p = 0.092 | p = 0.448 | A |
| | | | | | | p = 0.230 | p = 0.942 | p = 0.442 | C |
| HF | 0.39 ± 0.06 | 0.43 ± 0.09 | p = 0.701 | 0.43 ± 0.06 | p = 0.414 | | | | |
| LF | 0.35 ± 0.05 | 0.22 ± 0.03 | p < 0.05 | 0.36 ± 0.08 | p = 0.858 | | | | |
| Sham | 0.39 ± 0.05 | 0.38 ± 0.08 | p = 0.486 | 0.36 ± 0.03 | p = 0.340 | | | | |
| Prolactin (ng/mL) | | | | | | p = 0.576 | p = 0.660 | p = 0.949 | A |
| | | | | | | p = 0.388 | p = 0.205 | p < 0.05 | C |
| HF | 17.1 ± 1.3 | 10.8 ± 0.9 | p < 0.001 | 17.6 ± 2.0 | p = 0.771 | | | | |
| LF | 15.8 ± 2.0 | 10.2 ± 1.8 | p < 0.0001 | 12.3 ± 1.2 | p = 0.171 | | | | |
| Sham | 15.0 ± 2.5 | 9.2 ± 1.7 | p < 0.01 | 14.2 ± 1.3 | p = 0.215 | | | | |

Body Weight

The weight variation, as measured at baseline, visit 15, FU1 FU2 and FU3 is presented in Table 4 and FIG. 20B.

After 15 repetitive dTMS sessions, a significant weight loss was observed in all 3 groups: HF (−4.1±0.6% vs baseline, p=0.00002), in LF (−2.3±0.8% vs baseline, p=0.013) and in Sham (−2.0±0.6% vs baseline, p=0.015), but comparing weight loss in HF and Sham, the decrease was significantly higher in HF (p=0.027); a trend to a higher weight loss was found in HF group compared to LF group (p=0.087).

Patients belonging to HF continued losing weight even after 4 weeks (−5.8±0.8% vs baseline, p=0.00001; p=0.036 vs Sham) and 6 months of follow-up (−4.9±1.4% vs baseline, p=0.006; p=0.024 vs LF group).

No significant differences in weight loss were found between the two sub-groups HF (cue) and HF (no cue) after 5 weeks of treatment (−4.8±1.0% vs −3.2±0.6%, p=0.201), and at the follow-up visits.

Out of the 33 enrolled patients, 14 were re-evaluated 1 year after the end of the treatment (FU3): HF continued losing weight (−7.2±2.6% vs baseline, p=0.040); LF gained weight (+5.7±5.1%, p=0.460); Sham did not significantly change (−1.4±0.8%, p=0.160). A trend to a higher weight loss was found in HF group compared to Sham (p=0.068).

In a similar way, after 15 dTMS sessions, a significant decrease in Body Mass Index (BMI) was found in HF (−4.0±0.6% vs baseline, p=0.00002), in LF (−2.2±0.8% vs baseline, p=0.024) and in Sham (−2.0±0.6% vs baseline, p=0.008), but the decrease in BMI was significantly higher in HF compared to Sham (p=0.036); a trend to a higher BMI decrease was found in HF group compared to LF group (p=0.084).

In HF, BMI significantly continued to diminish even after 4 weeks (−5.8±0.8% vs baseline, p=0.00001) and 6 months of follow-up (−4.9±1.5% vs baseline, p=0.007). BMI decrease was significantly higher in HF group compared to Sham at FU1 (p=0.027) and at FU2 (p=0.024) compared to LF.

No significant differences in BMI reduction were found between the two sub-groups HF (cue) and HF (no cue) after 5 weeks of treatment (−4.9±1.0% vs −3.1±0.6%, p=0.166), and at the follow-up visits.

TABLE 5

Acute and chronic variations of supplementary measured parameters

| | T0 | T1 | T0 vs T1 | T2 | T0 vs T2 | HF vs Sham | HF vs LF | LF vs Sham | |
|---|---|---|---|---|---|---|---|---|---|
| FCQ-T Score | | | | | | p = 0.236 | p = 0.190 | p = 0.975 | C |
| HF | 126.1 ± 10.6 | — | — | 70.9 ± 8.1 | p < 0.00001 | | | | |
| LF | 120.6 ± 14.9 | — | — | 81.3 ± 14.1 | p < 0.01 | | | | |
| Sham | 116.8 ± 12.7 | — | — | 73.7 ± 6.0 | p < 0.01 | | | | |
| FM (%) | | | | | | p = 0.933 | p = 0.512 | p = 0.564 | C |
| HF | 46.9 ± 4.8 | — | — | 45.2 ± 2.3 | p < 0.05 | | | | |
| LF | 49.9 ± 7.5 | — | — | 46.7 ± 2.7 | p = 0.718 | | | | |
| Sham | 46.0 ± 5.3 | — | — | 43.4 ± 2.1 | p = 0.654 | | | | |
| FFM (%) | | | | | | p = 0.911 | p = 0.430 | p = 0.563 | C |
| HF | 53.1 ± 5.3 | — | — | 55.0 ± 2.4 | p < 0.05 | | | | |
| LF | 50.1 ± 7.5 | — | — | 53.3 ± 2.7 | p = 0.718 | | | | |
| Sham | 54.0 ± 6.2 | — | — | 56.6 ± 2.1 | p = 0.229 | | | | |
| SBP (mm Hg) | | | | | | p = 0.910 | p = 0.237 | p = 0.376 | A |
| | | | | | | p = 0.195 | p = 0.451 | p = 0.054 | C |
| HF | 124.6 ± 2.9 | 117.7 ± 2.6 | p < 0.05 | 115.0 ± 3.2 | p = 0.05 | | | | |
| LF | 113.1 ± 4.3 | 111.1 ± 4.5 | p = 0.442 | 110.0 ± 4.2 | p = 0.253 | | | | |
| Sham | 121.1 ± 2.6 | 115.0 ± 4.4 | p = 0.171 | 106.3 ± 2.5 | p < 0.05 | | | | |
| DBP (mmHg) | | | | | | p = 0.365 | p = 0.273 | p = 0.716 | A |
| | | | | | | p = 0.445 | p = 0.361 | p = 0.750 | C |
| HF | 82.3 ± 1.8 | 80.0 ± 2.5 | p = 0.213 | 75.3 ± 2.6 | p < 0.01 | | | | |
| LF | 71.9 ± 4.4 | 71.1 ± 3.1 | p = 0.826 | 69.4 ± 2.4 | p = 0.535 | | | | |
| Sham | 73.3 ± 4.1 | 73.3 ± 4.1 | p = 1.000 | 67.5 ± 2.7 | p = 0.265 | | | | |
| Very Mild PAT (min/day) | | | | | | p = 0.133 | p = 0.875 | p = 0.229 | C |
| HF | 911.6 ± 55.5 | — | — | 878.0 ± 42.2 | p = 0.538 | | | | |
| LF | 947.3 ± 46.4 | — | — | 930.3 ± 56.7 | p = 0.794 | | | | |
| Sham | 746.0 ± 78.9 | — | — | 827.8 ± 110.3 | p = 0.131 | | | | |
| Mild PAT (min/day) | | | | | | p = 0.234 | p = 0.841 | p = 0.468 | C |
| HF | 15.1 ± 3.3 | — | — | 19.9 ± 3.3 | p < 0.05 | | | | |
| LF | 17.3 ± 3.7 | — | — | 22.7 ± 3.4 | p = 0.183 | | | | |
| Sham | 18.8 ± 4.5 | — | — | 21.2 ± 5.1 | p = 0.595 | | | | |
| Moderate PAT (min/day) | | | | | | p = 0.239 | p = 0.546 | p = 0.679 | C |
| HF | 3.2 ± 1.2 | — | — | 6.7 ± 3.7 | p = 0.234 | | | | |
| LF | 2.3 ± 1.0 | — | — | 4.0 ± 1.7 | p = 0.296 | | | | |
| Sham | 4.4 ± 1.6 | — | — | 4.8 ± 2.0 | p = 0.757 | | | | |
| Steps (steps/day) | | | | | | p = 0.093 | p = 0.702 | p = 0.169 | C |
| HF | 5085.3 ± 758.7 | — | — | 7263.6 ± 1251.3 | p = 0.070 | | | | |
| LF | 5507.5 ± 1042.9 | — | — | 7071.2 ± 919.9 | p = 0.096 | | | | |
| Sham | 6687.2 ± 1293.8 | — | — | 6779.8 ± 1211.8 | p = 0.923 | | | | |
| Cholesterol (mg/dL) | | | | | | p = 0.615 | p = 0.518 | p = 0.825 | A |
| | | | | | | p = 0.960 | p = 0.169 | p = 0.137 | C |
| HF | 197.4 ± 8.9 | 200.9 ± 8.6 | p = 0.061 | 189.9 ± 9.1 | p = 0.304 | | | | |
| LF | 207.7 ± 19.9 | 208.4 ± 18.2 | p = 0.837 | 177.4 ± 12.2 | p = 0.090 | | | | |
| Sham | 190.2 ± 6.1 | 195.1 ± 21.4 | p = 0.238 | 184.9 ± 7.1 | p < 0.05 | | | | |
| Triglycerides (mg/dL) | | | | | | p = 0.719 | p = 0.842 | p = 0.881 | A |
| | | | | | | p = 0.735 | p = 0.379 | p = 0.314 | C |
| HF | 155.4 ± 31.2 | 143.9 ± 28.2 | p = 0.076 | 122.0 ± 11.6 | p = 0.263 | | | | |
| LF | 174.9 ± 39.2 | 158.0 ± 30.0 | p = 0.237 | 132.1 ± 27.3 | p = 0.285 | | | | |
| Sham | 105.7 ± 13.6 | 95.8 ± 14.9 | p = 0.139 | 95.8 ± 7.9 | p = 0.551 | | | | |
| Glucagon (pg/mL) | | | | | | p = 0.976 | p = 0.281 | p = 0.164 | A |
| | | | | | | p = 0.759 | p = 0.432 | p = 0.169 | C |
| HF | 42.6 ± 4.1 | 42.6 ± 3.1 | p = 0.952 | 42.0 ± 3.7 | p = 0.998 | | | | |
| LF | 30.5 ± 4.3 | 35.7 ± 3.4 | p = 0.051 | 38.0 ± 3.3 | p = 0.080 | | | | |
| Sham | 40.9 ± 4.1 | 42.6 ± 6.2 | p = 0.529 | 38.9 ± 3.2 | p = 0.557 | | | | |
| Fructosamine (μmol/L) | | | | | | p = 0.728 | p = 0.906 | p = 0.808 | C |
| HF | 235.2 ± 6.4 | — | — | 237.9 ± 8.0 | p = 0.663 | | | | |
| LF | 227.3 ± 11.1 | — | — | 224.4 ± 8.4 | p = 0.809 | | | | |
| Sham | 236.2 ± 10.8 | — | — | 238.3 ± 3.2 | p = 0.671 | | | | |
| Ghrelin (ng/mL) | | | | | | p = 0.796 | p = 0.127 | p = 0.170 | A |
| | | | | | | p = 0.462 | p = 0.282 | p = 0.242 | C |

TABLE 5-continued

Acute and chronic variations of supplementary measured parameters

|  | T0 | T1 | T0 vs T1 | T2 | T0 vs T2 | HF vs Sham | HF vs LF | LF vs Sham | |
|---|---|---|---|---|---|---|---|---|---|
| HF | 13.5 ± 3.0 | 14.3 ± 2.8 | p = 0.552 | 12.0 ± 2.7 | p = 0.984 | | | | |
| LF | 14.9 ± 2.9 | 27.3 ± 8.1 | p = 0.085 | 12.7 ± 3.9 | p = 0.489 | | | | |
| Sham | 13.6 ± 4.4 | 15.1 ± 3.9 | p = 0.950 | 13.8 ± 4.1 | p = 0.943 | | | | |
| Epinephrine | | | | | | p = 0.393 | p = 0.686 | p = 0.448 | A |
| (pg/mL) | | | | | | p = 0.687 | p = 0.269 | p = 0.112 | C |
| HF | 359.7 ± 55.4 | 340.4 ± 44.5 | p = 0.604 | 389.9 ± 82.4 | p = 0.685 | | | | |
| LF | 290.5 ± 38.7 | 287.3 ± 37.9 | p = 0.702 | 247.0 ± 18.2 | p = 0.153 | | | | |
| Sham | 415.3 ± 125.6 | 373.7 ± 111.8 | p = 0.148 | 445.7 ± 117.1 | p = 0.634 | | | | |
| TSH | | | | | | p = 0.901 | p = 0.528 | p = 0.358 | A |
| (µUI/mL) | | | | | | p = 0.775 | p = 0.548 | p = 0.427 | C |
| HF | 2.72 ± 0.28 | 2.09 ± 0.21 | p < 0.01 | 2.55 ± 0.28 | p = 0.391 | | | | |
| LF | 2.68 ± 0.59 | 1.99 ± 0.41 | p < 0.05 | 2.44 ± 0.53 | p = 0.375 | | | | |
| Sham | 3.14 ± 0.59 | 2.86 ± 0.57 | p < 0.01 | 2.66 ± 0.58 | p = 0.361 | | | | |
| ACTH | | | | | | p = 0.689 | p = 0.753 | p = 0.471 | A |
| (pg/mL) | | | | | | p = 0.482 | p = 0.751 | p = 0.369 | C |
| HF | 27.3 ± 3.5 | 23.3 ± 4.9 | p = 0.402 | 25.4 ± 3.8 | p = 0.521 | | | | |
| LF | 28.1 ± 2.8 | 20.3 ± 2.8 | p = 0.073 | 23.2 ± 2.6 | p = 0.251 | | | | |
| Sham | 27.8 ± 3.5 | 25.3 ± 3.5 | p = 0.435 | 26.9 ± 3.8 | p = 0.631 | | | | |
| FSH | | | | | | p = 0.848 | p = 0.505 | p = 0.620 | A |
| (mUI/mL) | | | | | | p = 0.820 | p = 0.899 | p = 0.752 | C |
| HF | 16.5 ± 6.3 | 17.0 ± 6.6 | p = 0.203 | 19.1 ± 7.9 | p = 0.199 | | | | |
| LF | 15.9 ± 5.8 | 15.7 ± 5.8 | p = 0.599 | 18.1 ± 6.6 | p = 0.814 | | | | |
| Sham | 23.6 ± 8.4 | 26.0 ± 8.5 | p = 0.719 | 28.4 ± 9.7 | p = 0.092 | | | | |
| LH | | | | | | p = 0.827 | p = 0.903 | p = 0.811 | A |
| (mUI/mL) | | | | | | p = 0.452 | p = 0.447 | p = 0.835 | C |
| HF | 10.7 ± 3.2 | 11.1 ± 3.3 | p = 0.396 | 11.8 ± 3.0 | p = 0.478 | | | | |
| LF | 12.6 ± 4.3 | 11.3 ± 3.9 | p = 0.116 | 12.6 ± 4.4 | p = 0.766 | | | | |
| Sham | 15.9 ± 4.3 | 17.6 ± 4.7 | p = 0.829 | 19.4 ± 5.7 | p = 0.286 | | | | |

Body Composition

As to body composition parameters evaluated by plethysmography (Table 5), a significant decrease in Fat Mass (FM) percentage (−2.0±0.7% vs baseline, p=0.017) was found in HF, after 5 weeks of treatment. However, no significant difference in the FM variation was found compared to other groups. Conversely, Fat Free Mass (FFM) percentage significantly increased in HF after 5 weeks of treatment (+2.4±0.7% vs baseline, p=0.018). No significant difference in the FFM variation was found compared to other groups.

No significant changes in FM and FFM were shown at the 6-month follow-up.

Resting Energy Expenditure (REE) and Respiratory Quotient (RQ)

Figure 21:
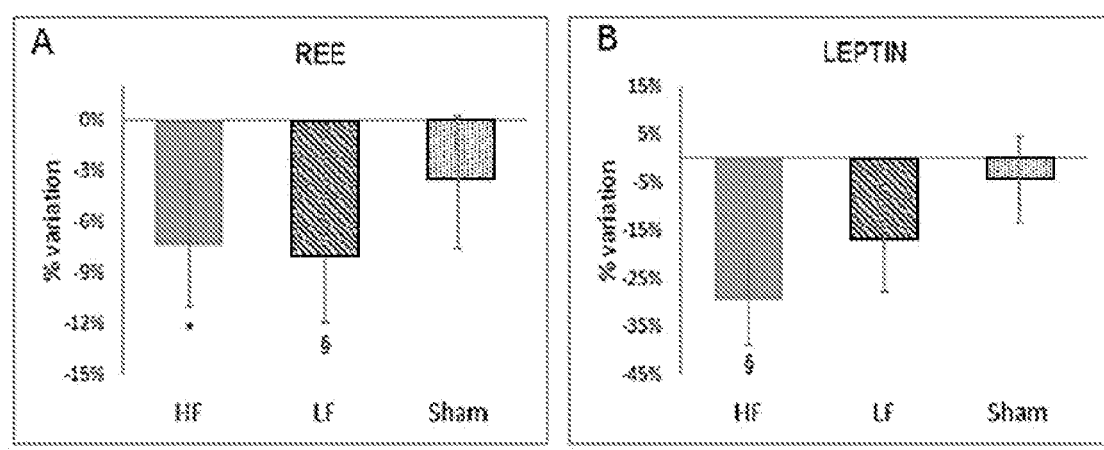
FIGS. 21a and 21b show the effects of magnetic stimulation on metabolic and hormonal parameters of obese subjects.

As to the metabolic parameters evaluated by indirect calorimetry (Table 4), in the HF the REE percentage significantly decreased at the end of treatment (−7.4±3.6% vs baseline, p=0.030); a trend toward significant decrease was observed in LF (−8.0±4.0% vs baseline, p=0.073) (FIG. 21A). These variations were not significant compared to other groups and did not persist at FU2.

A significant reduction of RQ between baseline and end of treatment was found both in the HF (−3.8±1.8% vs basal, p=0.040) and in LF (−7.4±2.1% vs baseline, p=0.014; p=0.055 vs Sham). No significant changes in RQ were found between baseline and the 6-month follow-up visit.

Blood Pressure and Heart Rate

After a single dTMS session, a significant decrease of Systolic Blood Pressure (SBP) (−5.2±2.1% vs baseline, p=0.02) (Table 5) and heart rate (−5.6±1.7% vs baseline, p=0.009) (Table 4) were found in HF. No significant acute variation was observed for Diastolic Blood Pressure (DBP) (Table 5).

After 5 weeks of dTMS treatment, a significant decrease of SBP was found both in the HF (−5.8±2.9% vs baseline, p=0.05) and in the Sham (−11.9±3.5% vs baseline, p=0.01) without significant differences between the two groups; after 15 dTMS sessions, DBP significantly decreased only in HF (−7.7±2.4% vs baseline, p=0.006). Chronically, no significant differences in hearth rate were observed within and between groups.

Activity Energy Expenditure (AEE)

Out of the 33 enrolled patients, 20 (HF n=9; LF n=6; Sham n=5) underwent an evaluation of the AEE during the 5 weeks of treatment. See Tables 4 and 5, and FIG. 22.

An increasing trend in AEE was observed both in HF (+56.2±22.5% vs baseline, p=0.043; p=0.07 vs Sham) and in LF (+49.2±25.3% vs baseline, p=0.089); consequently, a trend to increase Total Energy Expenditure (TEE) was observed in both groups (HF: +4.9±2.3% vs baseline, p=0.049; LF: +4.7±1.9% vs baseline, p=0.052).

After 5 weeks of treatment, the average daily activity time increased in HF (+73.9±21.1% vs baseline, p=0.059); specifically, mild physical activity time [3-4 Metabolic Equivalent of Tasks (METs)] significantly increased (+58.6±22.0% vs baseline, p=0.033).

Moreover, in HF a significant increase of METs (+18.0±5.9% vs baseline, p=0.034; p=0.08 vs Sham), a trend to increase the average daily steps (+51.1±22.7% vs baseline, p=0.070), and the average distance (+49.6±22.0% vs baseline, p=0.073; p=0.069 vs Sham) were noted.

No significant differences in very mild, moderate, and intensive physical activity time were found either within each group, or between groups.

Metabolic and Neuro-Endocrine Assessments

Acute and chronic variations of laboratory measurements are presented in Tables 4 and 5.

Acute Effects of dTMS

Figure 23:
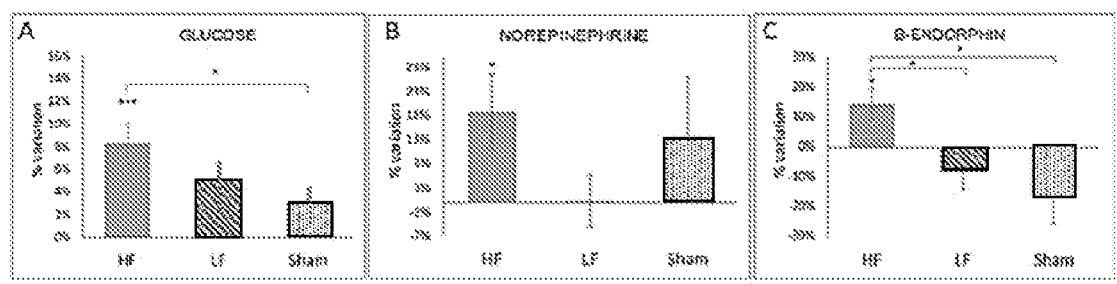
FIGS. 23a, 23b and 23c show the acute effects of magnetic stimulation on the patients' neuro-metabolic parameters.

A significant increase in glucose was found in HF (+8.2±1.9% vs baseline, p=0.0004) comparing blood glucose levels before (T0) and immediately after the first dTMS session (T1). Glucose rise was significantly higher in HF compared to Sham (p=0.029) (FIG. 23A). In addition, a trend to increase in cholesterol level was observed in the HF (+2.0±0.9% vs baseline, p=0.061). As to the neurotransmitters, a significant increase in norepinephrine levels (+18.8±7.7% vs baseline, p=0.015; p=0.064 vs LF) was found after a single HF dTMS session (FIG. 23B). A significant rise of β-endorphin levels (+14.3±5.4% vs baseline, p=0.045) was detected only in HF; it was significant compared to both Sham (p=0.024) and LF (p=0.014) (FIG. 23C). A decreasing trend in β-endorphin levels was actually observed in these groups.

Leptin levels significantly decreased between T0 and T1 in HF (−16.3±3.0% vs baseline, p=0.002).

A trend to reduction in insulin levels (−11.0±5.6% vs baseline, p=0.073) and a trend to increase in glucagon levels (+12.4±5.8% vs baseline, p=0.051) were found after a single LF dTMS session. No significant variations in insulin levels were found in HF.

In all three groups, a significant reduction in the pituitary hormones Thyroid Stimulating Hormone (TSH) (HF: −20.7±5.3% vs baseline, p=0.003; LF: −24.7±3.3% vs baseline, p=0.010; Sham: −19.9±3.8% vs baseline, p=0.007) and prolactin (HF: −34.1±5.1% vs baseline, p=0.0001; LF: −37.1±4.2% vs baseline, p=0.00004; Sham: −37.4±2.7% vs baseline, p=0.0038) were found after a single dTMS session, without significant differences among groups. In LF, a trend to decrease in Adreno-Cortico-Tropic Hormone (ACTH) levels was observed (−17.7±17.3% vs baseline, p=0.073). A significant reduction of cortisol levels (−29.3±10.4% vs baseline, p=0.023) was found after a single LF dTMS session.

Triglycerides, ghrelin, Follicle-Stimulating Hormone (FSH), Luteinizing Hormone (LH), epinephrine did not show significant changes after a single dTMS session.

Chronic Effects of dTMS

Concerning the following metabolic parameters: glucose, cholesterol, triglycerides, neither significant chronic variations within groups nor differences between groups were shown.

Comparing baseline values (T0) with values before the last dTMS session (T2), a trend to significant reduction was found for insulin (−6.6±13% vs baseline, p=0.086) and HOmeostatic Model Assessment of Insulin Resistance (HOMA-IR) index (−7.3±13.9% vs baseline, p=0.074) in HF. A significant reduction of glycated hemoglobin was found between T0 and T2 (−7.7±1.3% vs baseline, p=0.003; p=0.075 vs LF) in the same group; it persisted up to FU1 (−8.1±1.4% vs baseline, p=0.024). Fructosamine did not show significant changes in any group after 15 dTMS sessions and at follow-up visits.

Comparing baseline leptin levels between T0 and T2, a trend to decrease in HF (−29.5±9.2%, p=0.062) was observed (FIG. 21B), the reduction became significant after 1 month of follow-up (−32.3±10.6%, p=0.009) and persisted also at the FU3 visit (−38.3±19.2%, p=0.058; p=0.043 vs Sham; p=0.016 vs LF). Ghrelin levels did not show significant chronic changes in all three groups.

Neither significant chronic (between T0 and T2) variation within each group nor differences between groups were shown in relation to epinephrine, norepinephrine, β-endorphin, TSH, ACTH and salivary cortisol.

In LF, prolactin levels decreased between T0 and T2 significantly compared to Sham (−11.1±7.1% vs +13.2±6.8%, p=0.027), and continued up to FU1 (−18.2±10.3% vs baseline, p=0.093) and FU3 (−26.4±1.3% vs baseline, p=0.020).

Adverse Events and Safety

No serious or severe side effects leading to the interruption of the treatment were observed. Obese subjects who received HF dTMS experienced more frequent headache (9/33) than LF (4/33) and Sham groups (3/33). This side effect resolved spontaneously within 1-2 days from the beginning of treatment. There were no significant differences among the groups in the frequency and intensity of other reported adverse events: drowsiness (HF: 1/33, LF: 2/33, Sham: 1/33), neck pain (HF: 2/33, LF: 1/33, Sham: 2/33), temporary hypertension (HF: 1/33, LF: 1/33, Sham: 1/33).

This study examined the effects of multiple treatment sessions with dTMS over the PFC and insula, bilaterally, using either high- or low-frequency stimulation in obese humans. In addition, the study investigated acute and chronic modifications induced by repetitive dTMS on neuroendocrine pathways related to appetite/satiety balance. Chronic effects of repetitive dTMS on daily physical activity, resting energy expenditure, and body composition were also assessed. This is the first clinical study utilizing dTMS in obesity that demonstrates a decrease in body weight with an indication for a long-lasting weight control effect (at least 6 months). This effect occurred in obese patients receiving 15 daily sessions of HF stimulation. Several mechanisms could be involved in the pronounced weight lowering effects produced by the HF stimulation.

It was demonstrated that PFC (specifically DLPFC) is centrally implicated in inhibitory control processes and linked to self-control in the dietary context. These findings build on previous evidences that excitatory stimulation of DLPFC enhances inhibitory capacity and thereby alters habits, especially in substance and food addicted subjects. One mechanism potentially explaining the therapeutic effect of HF repetitive dTMS in obesity is the modulation of the mesolimbic dopamine system, or "reward system", which is implicated in the regulation of hedonic eating behavior. Dopamine signaling is involved in the "wanting" or desire of certain types of food, which underlie food craving. After 15 dTMS sessions, HF group showed a significant reduction of food craving, associated with a significant weight loss. This result indicates the modulation of the dopaminergic reward system as the principal mechanism by which dTMS affects the control of food craving. The demonstrated facilitation effect of repetitive TMS on DA release could be a result of a direct stimulation of the cortico-striatal axons, an indirect trans-synaptic activation of cortico-striatal neurons due to a reduction of GABA-mediated intra-cortical inhibition. It is plausible that the dTMS-induced effect on dopaminergic system "mimics" the effect of food on these pathways, while participants are in a food restriction diet.

In addition to dopamine, endogenous opioid compounds are also involved in the "reward system", mainly in the pleasurable feeling ("liking") associated with the food rewarding stimuli. Particularly, the β-endorphins secreted by the anorexigenic pro-opiomelanocortin (POMC) neurons in the hypothalamic arcuate nucleus, inhibit further POMC activation, leading to a decreased appetite and increased energy expenditure. Interestingly, in our study, after a single HF dTMS session a significant increase of β-endorphins compared to baseline and other groups was found. This finding suggests, on the one hand, an endogenous opioids-induced activation of the DA system leading to DA release ("dopamine cascade"), on the other hand a role of dTMS in modulating hypothalamic hunger through a negative feedback of β-endorphins on POMC neurons. This dual effect of dTMS in regulating both "hedonic hunger" (reward system modulation) and "homeostatic hunger" (hypothalamic regulation) could explain the longer lasting action (at least 6 months) of HF dTMS in reducing food craving, compared to LF or sham stimulation. Moreover, a potential action of dTMS on neuroplasticity (e.g. DA transporter availability), as recently suggested by a study of dTMS in alcoholism, could unfold the long-lasting effect of HF dTMS in decreasing food craving.

No significant effects of dTMS on body weight were observed in the LF, as previously stated in a clinical trial testing the efficacy of dTMS in smoking. LH stimulation 1 Hz) has been shown to inhibit cortical excitability. Although the LH repetitive TMS has proven to be effective and safe in the treatment of certain diseases such as depression, it reported poor results in the treatment of addiction. It has been suggested that suppression of the left DLPFC activity by LF repetitive TMS reduces its inhibitory control, leading to enhance cue-induced craving for drugs, as observed in methamphetamine-dependent patients. Our results are consistent with this model and could explain the lack of dTMS effects in LF group.

In this study, no disadvantage or advantage in weight loss has been found when stimulating the subjects with pictures of favorite food just prior to the high-frequency stimulation treatment, in contradiction with previous TMS studies. Substances versus neutral cues exposure demonstrated activation in a wide variety of expected brain regions, which are known to be involved in the mechanisms of substances and food craving. Therefore, exposure to substance cues leads to an increase in craving despite the motivation to remain abstinent. It has been argued that by repeating exposure and avoiding substance intake, the cues lose their predictive value, and hence craving gradually extinguishes. In this study, the lack of difference between the subgroups that received or did not receive the cueing procedure leads to suppose that craving reduction is not secondary to an extinction mechanism after repeated cues exposure, but a primary effect of dTMS on food craving reduction. Moreover, in our study the cueing procedure was performed by showing pictures of the most favorite type of food, rather than actual food.

Figure 22:
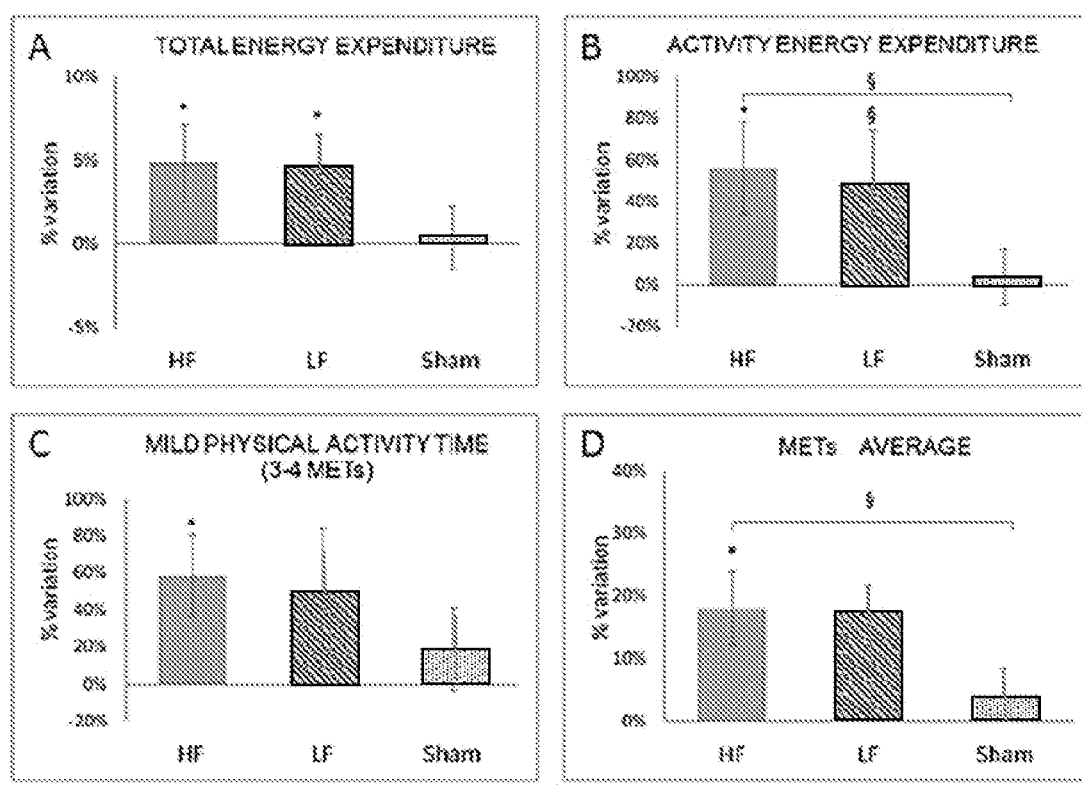
FIGS. 22a, 22b, 22c and 22d show the chronic effects of magnetic stimulation on the patients' physical activity.

Physical activity is normally defective in obese subjects. Nonetheless a life-style intervention beyond dietary counseling is mandatory to achieve and maintain weight reduction. Voluntary contraction of skeletal muscle fibers are regulated by effective cortical areas, including motor areas and pre-frontal cortex. Sympathetic activation increases frequency, intensity and strength of skeletal muscle contractile activity. Intracerebral administration of DA agonists or of DA antagonists respectively activates and inhibits locomotor activity in rats. It has been demonstrated in the D2R knockdown mouse model that low DA D2 receptor increases vulnerability to obesity via reduced physical activity rather than via increased appetitive motivation. The present data demonstrate that HF dTMS increases locomotor activity over a 5-weeks period (FIG. 22). Since several reports suggested that HF TMS increases the concentration of endogenous DA in the striatum, and in the Broadmann area 11 of the medial orbitofrontal cortex, it is conceivable that at least part of the weight-lowering effect of our treatment is related to direct activation of locomotor activity in the obese subjects. Moreover, the observed increase of norepinephrine after a single HF dTMS suggests a role of stimulation-induced sympathetic system activation in increasing physical activity.

Resting Energy Expenditure was assessed in all patients at the beginning of the study, after 5 weeks of treatment and after 6 months of follow up. After 5 weeks, REE (%) significantly decreased in HF group but this reduction did not continue up to the follow-up visits. This effect could be explained by the higher weight loss observed in this group; it is well known that loss of body weight with energy restriction consistently results in a lower REE (40). Moreover, a significant reduction of RQ between baseline and end of treatment was found in the HF and in LF groups. The improvement of respiratory quotient may be interpreted as a consequence of improved fat oxidation during weight reduction. Acute and chronic modifications of neuro-endocrine pathways, related to the appetite/satiety balance, were evaluated in this study to identify the neurophysiological mechanisms involved in food reward and craving and the effects of dTMS. Interestingly, after the first dTMS session a significant increase of glucose (FIG. 23), and a significant decrease of leptin were found in the HF group. Acute leptin reduction after a single HF dTMS session is consistent with previous observations which provided indirect evidence for an inhibitory effect of dopaminergic neurotransmission on leptin secretion. The previous hypothesis of an increase of dopaminergic activity in the mesolimbic and mesostriatal pathways after HF dTMS is also indirectly sustained by the findings of decreased leptin levels. In turn, leptin is implicated in glucose homeostasis, particularly in the control of peripheral tissue insulin sensitivity. In non-diabetic rats, an acute intravenous (i.v.) leptin infusion enhanced insulin's ability to suppress glucose production. The decrease of leptin level after 5 weeks of treatment and the decrease of insulin and HOMA-IR indicate an overall metabolism improvement following the dTMS treatment.

In conclusion, this study indicates that HF dTMS over the lateral PFC and insula reduces food craving and body weight with significant and long-lasting effects via several mechanisms. It is conceivable that the main mechanism is the increased dopaminergic activity in the mesolimbic and mesostriatal pathways, inducing a control on food craving and intake, as well as on physical activity Furthermore, identifying acute and chronic modifications of neuro-endocrine pathways related to the appetite/satiety balance allowed to improve knowledge of neurophysiological mechanisms involved in food reward and craving. Finally, the safety of the methodology reported in this study allows for the treatment to be repeated over the years in the same obese subject.

Those skilled in the art may make several changes and variations to the method and system described above in order to meet specific and incidental needs, all falling within the scope of protection of the present invention as defined in the appended claims.

The invention claimed is:

1. A method for a deep and repetitive transcranial magnetic stimulation of an individual by means of magnetic pulses applied to a region of a scalp of the individual, said region being at least the a bilateral prefrontal cortex, the method comprising the following steps:
   determining a threshold intensity of said magnetic pulses by applying to the individual one or more reference magnetic stimulations and determining a reaction of the individual to said one or more reference magnetic stimulations, wherein said reaction corresponds to a right thumb movement; and
   repeatedly applying a magnetic stimulation for at least 80 application trains per session of a duration not exceeding 2 seconds each with one time interval between an application train and the next one no less than 20 seconds, wherein said magnetic stimulation has a frequency of at least 18 Hz with an intensity of stimulation of at least 120% of threshold intensity, wherein the step of determining a threshold intensity comprises:

applying the one or more reference magnetic stimulations to a scalp region of the individual corresponding to a primary motor cortex, and decreasing an intensity of the one or more reference magnetic stimulations at regular intervals until obtaining the threshold intensity corresponding to a lowest stimulation intensity needed to determine said reaction of the individual.

2. The method according to claim 1, further comprising a step of measuring the temperature of the individual through an infrared thermography unit in an interscapular region of said individual to determine a dopaminergic activation.

3. The method according to claim 2, wherein the temperature of the individual in the interscapular region increases selectively by at least 1° C. after a repeated application of magnetic stimulation for a treatment less than 30 minutes.

4. The method of claim 1, wherein said region includes an insula.

5. A method for modulating a composition of a microbiota of an individual comprising the following steps:

determining a threshold intensity of magnetic pulses by applying to the individual one or more reference magnetic stimulations and determining a reaction of the individual to said one or more reference magnetic stimulations, wherein said reaction corresponds to a right thumb movement; and repeatedly applying a magnetic stimulation for at least 80 application trains per session of a duration not exceeding 2 seconds each with one time interval between an application train and the next one no less than 20 seconds, wherein said magnetic stimulation has a frequency of at least 18 Hz with an intensity of stimulation of at least 120% of threshold intensity, wherein the step of determining a threshold intensity comprises:

applying the one or more reference magnetic stimulations to a scalp region of the individual corresponding to a primary motor cortex, and decreasing an intensity of the one or more reference magnetic stimulations at regular intervals until obtaining the threshold intensity corresponding to a lowest stimulation intensity needed to determine said reaction of the individual.

6. The method according to claim 5, wherein the microbiota is enriched with bacteria having anti-inflammatory and/or adjuvant properties of intestinal metabolism.

7. The method according to claim 6 wherein said bacteria belong to the *Faecalibacterium* and/or *Alistipes* genera.

8. A system for the deep and repetitive transcranial magnetic stimulation of an individual by means of magnetic pulses applied at least to a scalp region of the individual, said region being at least the a bilateral prefrontal cortex, the system comprising:

stimulation means for generating and applying a magnetic stimulation, said means comprising a pulse generator of magnetic pulses and stimulating elements; and computer hardware and software for managing and controlling the magnetic stimulation, wherein said computer hardware and software are configured to:

determine a threshold intensity of the magnetic pulses by applying to the individual one or more reference magnetic stimulations, determine a reaction of the individual to said one or more reference magnetic stimulations, wherein said reaction corresponds to a movement of the right thumb, and manage the stimulation means so as to perform, after the determination of the threshold intensity, the magnetic stimulation comprising at least 80 application trains per session of a duration not exceeding 2 seconds each with a time interval between an application train and the next one not less than 20 seconds, said magnetic stimulation having a pulse frequency of at least 18 Hz and a stimulation intensity of at least 120% of the threshold intensity, wherein the step of determining a threshold intensity comprises:

applying the one or more reference magnetic stimulations to a scalp region of the individual corresponding to a primary motor cortex, and decreasing an intensity of the one or more reference magnetic stimulation at regular intervals until obtaining the threshold intensity corresponding to a lowest stimulation intensity needed to determine said reaction of the individual.

9. The system according to claim 8, wherein the stimulation means comprise an "H"-shaped coil for deep transcranial magnetic stimulation.

10. The system according to claim 8, further comprising an infrared thermography unit for detecting a selective temperature increase of the skin of the individual and means for measuring movement of the individual, wherein said means for measuring movement of the individual is an accelerometer.

11. A method for regulating glucose metabolism and/or reducing blood glucose levels of an individual by deep and repetitive transcranial magnetic stimulation by means of magnetic pulses applied at least to a region of a scalp of the individual, said region being at least a bilateral prefrontal cortex, wherein the method initially comprises determining a threshold intensity of the magnetic pulses by applying to the individual one or more reference magnetic stimulations and determining a reaction of the individual to said one or more reference stimulations, wherein said reaction corresponds to a movement of a right thumb and subsequently a repeated application of a magnetic stimulation at a pulse frequency greater than or equal to 1 Hz with an intensity greater than said threshold intensity, wherein said method is not aimed at reducing an individual's dependence on a particular substance or habit, and wherein the threshold intensity determination occurs by applying the one or more reference magnetic stimulations to a scalp area corresponding to a primary motor cortex at regular intervals gradually decreasing an intensity of said one or more reference stimulations until obtaining the threshold intensity corresponding to a lowest stimulation required to determine said reaction of the individual.

12. The method according to claim 11, wherein the repeated application of the magnetic stimulation modulates a regulation of the an activity of a sympathetic nervous system and/or causes a change in a level of hormones selected from the group consisting of insulin, leptin, adrenaline and ghrelin in the individual.

13. The method according to claim 11, wherein the repeated application of the magnetic stimulation occurs at a frequency of at least 18 Hz with a stimulation intensity of at least 120% of the threshold intensity.

14. The method according to claim 13, wherein the repeated application of magnetic stimulation comprises at least 80 application trains per session, each having a duration of no more than 2 seconds with a time interval between a train application and the next one no less than 20 seconds.

15. The method according to claim 11, wherein the magnetic stimulation is applied to an area of the scalp of the individual to indirectly influence a cerebral area corresponding to an arcuate nucleus by induction of electric current in said cerebral area as a consequence of the stimulation of a prefrontal cortex and insula.

16. The method of claim 11, wherein said region includes an insula.

\* \* \* \* \*